(12) United States Patent
Stubbs et al.

(10) Patent No.: US 7,220,220 B2
(45) Date of Patent: May 22, 2007

(54) EXERCISE MONITORING SYSTEM AND METHODS

(76) Inventors: Jack B. Stubbs, 4266 Laura Marie Dr., Waynesville, OH (US) 45068; Kevin L. Schwieger, 633 W. Turtle Creek Rd., Lebanon, OH (US) 45036

( * ) Notice: Subject to any disclaimer, the term of this patent is extended or adjusted under 35 U.S.C. 154(b) by 90 days.

(21) Appl. No.: 10/847,208

(22) Filed: May 17, 2004

(65) Prior Publication Data
US 2004/0260191 A1 Dec. 23, 2004

Related U.S. Application Data

(62) Division of application No. 09/436,515, filed on Nov. 9, 1999, now Pat. No. 6,736,759.

(51) Int. Cl.
*A63B 21/00* (2006.01)
*A61B 5/00* (2006.01)

(52) U.S. Cl. .................. 482/72; 482/1; 482/8; 600/301; 600/520

(58) Field of Classification Search ............... 482/1–9, 482/72, 900–903; 600/300, 301, 481–484, 600/520
See application file for complete search history.

(56) References Cited

U.S. PATENT DOCUMENTS

| | | | |
|---|---|---|---|
| 4,273,113 A * | 6/1981 | Hofstein | .................. 601/29 |
| 4,566,461 A | 1/1986 | Lubell et al. | |
| 5,081,991 A | 1/1992 | Chance | |
| 5,148,002 A | 9/1992 | Kuo et al. | |
| 5,167,230 A | 12/1992 | Chance | |
| 5,318,487 A | 6/1994 | Golen et al. | |
| 5,345,244 A | 9/1994 | Gildea et al. | |
| 5,408,444 A | 4/1995 | Kita et al. | |
| 5,456,262 A | 10/1995 | Birnbuam | |
| 5,458,548 A | 10/1995 | Crossing et al. | |
| 5,464,021 A | 11/1995 | Birnbaum | |
| 5,486,818 A | 1/1996 | Loponen | |
| 5,491,474 A | 2/1996 | Suni et al. | |
| 5,564,417 A | 10/1996 | Chance | |
| 5,575,284 A | 11/1996 | Athan et al. | |
| 5,589,835 A | 12/1996 | Gildea et al. | |
| 5,611,346 A | 3/1997 | Heikkila et al. | |
| 5,622,180 A | 4/1997 | Tammi et al. | |
| 5,627,548 A | 5/1997 | Woo et al. | |
| 5,632,279 A | 5/1997 | Heikkila | |
| 5,690,119 A | 11/1997 | Rytky et al. | |
| 5,731,757 A | 3/1998 | Layson, Jr. | |
| 5,779,631 A | 7/1998 | Chance | |
| 5,781,155 A | 7/1998 | Woo et al. | |
| 5,810,722 A | 9/1998 | Heikkila | |
| 5,840,039 A | 11/1998 | Heikkila | |
| 5,852,401 A | 12/1998 | Kita | |

(Continued)

FOREIGN PATENT DOCUMENTS

WO WO9812599 3/1998

(Continued)

*Primary Examiner*—Glenn E. Richman
(74) *Attorney, Agent, or Firm*—Dinsmore & Shohl LLP

(57) ABSTRACT

An exercise monitoring system which includes an electronic positioning device; a physiological monitor; and a display unit configured for displaying data provided by said electronic positioning device and said physiological monitor.

20 Claims, 10 Drawing Sheets

U.S. PATENT DOCUMENTS

| | | |
|---|---|---|
| 5,884,198 A | 3/1999 | Kese et al. |
| 5,889,493 A | 3/1999 | Endo |
| 5,891,042 A | 4/1999 | Sham et al. |
| 5,905,460 A | 5/1999 | Odagiri et al. |
| 5,919,133 A | 7/1999 | Taylor et al. |
| 6,002,982 A * | 12/1999 | Fry .................. 701/213 |
| 6,013,007 A | 1/2000 | Roots et al. |
| 6,027,429 A * | 2/2000 | Daniels ................ 482/5 |
| 6,032,108 A | 2/2000 | Seiple et al. |
| 6,083,248 A | 7/2000 | Thompson |
| 6,148,262 A | 11/2000 | Fry |
| 6,148,280 A | 11/2000 | Kramer |
| 6,152,856 A | 11/2000 | Studor et al. |
| 6,199,550 B1 | 3/2001 | Wiesmann et al. |
| 6,285,314 B1 | 9/2001 | Nagatsuma et al. |
| 6,450,922 B1 * | 9/2002 | Henderson et al. ............ 482/8 |

FOREIGN PATENT DOCUMENTS

| | | |
|---|---|---|
| WO | WO9923524 | 5/1999 |
| WO | WO9923525 | 5/1999 |
| WO | WO0141879 | 6/2001 |

* cited by examiner

EXERCISE MONITORING SYSTEM AND METHODS

RELATED APPLICATIONS

The present application is a Divisional of U.S. application Ser. No. 09/436,515 filed Nov. 9, 1999 now U.S. Pat. No. 6,736,759. The entire disclosure of which is hereby incorporated by reference.

BACKGROUND OF THE INVENTION

1. Field of the Invention

The present invention relates to a monitoring system for use in a variety of physical activities, as well as training and analytical methods for physical activities. The present invention provides monitoring systems having an electronic positioning device and/or a physiological monitor (such as an oximeter or a heart rate monitor) in order to provide information concerning a subject performing a physical activity.

2. Description of Related Art

Throughout the world, more and more people are exercising in order to improve their general health and physical fitness. For the average person, however, a lack of motivation can significantly hinder their efforts. In addition, the natural tendency is to try and achieve the greatest results in the shortest possible time. When typical measurements of physical fitness and progress such as weight loss are monitored, however, expectations often are not met. The result can be a lack of motivation, which in turn leads to a cessation of exercise.

While athletes of all ages are usually able to overcome motivational hurdles, athletes often have difficulty in accurately measuring their progress. Human nature demands instantaneous feedback for motivation and encouragement. In addition, many athletes also do not know how to train effectively for maximal improvement. For example, competitive runners may have difficulty determining whether their pace on a particular day of training is too fast or too slow. While running on a track or treadmill may allow the runner to monitor his or her speed, speed alone is often an inadequate way to monitor optimal training levels.

Currently, there are essentially three methods of providing feedback to individuals engaged in a physical activity. The first, competition, can provide feedback concerning the individual's past training efforts in a particular physical activity. Competition feedback, however, is provided long after the training regimen has been completed, and therefore only allows for adjustments in subsequent training. In addition, many individuals are only interested in improving their general health and physical fitness rather than competing against others.

Another method of providing feedback to an individual engaged in a physical activity is heart rate monitoring. Heart rate monitors have become common place in the exercise industry and entire training programs have been developed based upon the data provided by these monitors. Typically, an ECG-type sensor is worn by the individual (such as in a strap which extends about the individual's chest), and heart rate (in beats per minute) is displayed on a wrist-watch type unit. While heart rate monitoring is a useful tool, heart rate data can be difficult to interpret. In addition, many individuals often resort to standardized tables in order to determine target heart rate training zones. Such standardized tables, however, only provide generalized guidelines which may or may not be appropriate for a particular individual or a particular physical activity.

The third feedback technique which may be used by individuals performing a physical activity is lactate monitoring. Lactate is a byproduct of the anaerobic metabolic process by which energy is produced in the body. The amount of lactate present in an individual's bloodstream provides an indication of their level of exertion. While lactate monitoring can be a valuable tool, it requires drawing blood samples which are analyzed by an expensive, electronic device. Thus, lactate monitoring is invasive, costly, and generally only useful for experienced athletes and their coaches.

SUMMARY OF THE INVENTION

Figure 1:
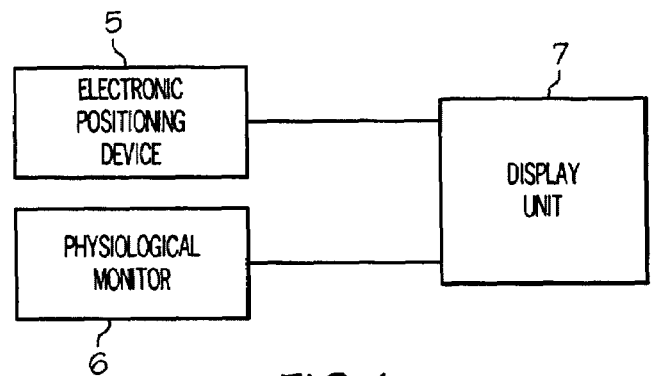
FIG. 1 is a schematic illustration of an exercise monitoring system according to one embodiment of the present invention.

One embodiment of the present invention is an exercise monitoring system which comprises:
a. an electronic positioning device;
b. a physiological monitor; and
c. a display unit (or component) configured for displaying data provided by the electronic positioning device and the physiological monitor.

The electronic positioning device is configured to receive electromagnetic signals from three or more sources so that the monitoring system can determine at least one of a subject's location, altitude, velocity, pace, and distance traveled. In one particular embodiment, the electronic positioning device comprises a GPS device. The physiological monitor may be chosen from the group consisting of: an oximeter and a heart rate monitor.

The electronic positioning device and the physiological monitor may be provided as part of a user-wearable data acquisition unit (or component) which is separate from the display unit. The data acquisition unit may further include a support member, wherein the electronic positioning device and the physiological monitor are provided on the support member. In one embodiment, the electronic positioning device and the physiological monitor are removably secured to the support member. The data acquisition unit may be configured to be worn by a subject in a variety of locations, such as the subject's waist or chest. The display unit may likewise be configured in a variety of manners. For example, the display unit may be configured to be worn about a human user's wrist, or may be configured to be mounted to a bicycle (e.g., mounted to the handlebars). The display unit may also comprise an external device to which the monitoring system of the present invention transmits data. For example, the monitoring system of the present invention may be configured to display acquired data on a personal computer ("PC"), and even store the data on the PC for later retrieval and analysis. The monitoring system may also be configured to display data on a treadmill display screen so that the monitoring system will provide blood oxygen data for a subject walking or running on a treadmill.

The physiological monitor of the exercise monitoring system may include a probe (or sensor) configured for acquiring physiological data from a user. The probe may be incorporated into the data acquisition component itself (such as integrally provided on or in the support member), or may comprise a separate unit which is in electrical communication with the data acquisition component (such as by means of a wire or cable, or by means of electromagnetic wave transmission). The monitoring system may further include at least one audible or visual alarms which is activated when data provided by at least one of the electronic positioning device and the physiological monitor does not meet a predetermined target (e.g., when the user's speed, blood oxygen level or heart rate exceeds or falls short of a predetermined target).

Another embodiment of the present invention is an exercise monitoring system which comprises:
a. an electronic positioning device configured to receive electromagnetic signals from three or more sources so that the monitoring system can determine a subject's velocity or pace;
b. a display unit configured for displaying data provided by the electronic positioning device; and
c. an alarm, wherein the alarm is activated when a subject's velocity or pace does not meet a predetermined target.

The electronic positioning device in this embodiment may comprise a GPS device.

Yet another embodiment of the present invention is an exercise monitoring system which comprises:
a. an oximeter configured to determine a subject's blood oxygen level;
b. a display unit configured for displaying the subject's blood oxygen level; and
c. an alarm, wherein the alarm is activated when the subject's blood oxygen level does not meet a predetermined target.

By way of example, the oximeter may comprise an oximetry probe and oximeter module, which are configured to acquire blood oxygen data by light absorption techniques. Preferably, the oximeters described herein are configured and positioned to determine systemic blood oxygen levels, rather than the blood oxygen level of targeted tissues or regions.

Another embodiment of the present invention is a method of controlling a subjects physical activity, comprising:
a. monitoring a subject's blood oxygen level while the subject performs a physical activity; and
b. maintaining the blood oxygen level at a selected level while the subject continues to perform the physical activity.

The subject may be human or animal (particularly horses, dogs, camels, and other mammals), and the monitoring step may even utilize the exercise monitoring systems described herein. It should be pointed out, however that blood oxygen data may also be acquired using conventional, readily-available oximeters. This method of controlling a subject's physical activity may be performed solely by the subject, or may involve another (such as a coach or trainer). In one particular embodiment, the method of controlling a subject's physical activity even provides a training method for athletes and the like using blood oxygen data.

The subject's blood oxygen level may be maintained at the selected level by adjusting the workload of the physical activity as necessary. In fact, the exercise monitoring systems described above may even be used for this purpose, since embodiments of the monitoring system can be configured for computing and displaying the subject's workload (based on the subject's velocity and weight, and optionally based on elevational changes). The subject's blood oxygen level may also be maintained at the selected level by adjusting the subject's level of exertion as necessary. As yet another alternative, the subject's blood oxygen level may be maintained at the selected (or predetermined) level by adjusting the subject's oxygen intake as necessary (e.g., by altering breathing patterns or methods, or by restricting or expanding oxygen or air intake). In fact, by limiting oxygen intake in order to reduce the subject's blood oxygen level athletic training (e.g., running or biking) at high altitude may be simulated.

The method of controlling a subject's physical activity is suitable for a variety of activities, including: walking, running, swimming, bicycling, skating, singing, skiing, boating, climbing, wheelchairing, snowshoeing, scuba diving, and flying. The step of monitoring blood oxygen level may comprise:
(a) providing an oximeter, the oximeter including a probe for non-invasively determining blood oxygen level (such as through light absorption measurements); and (b) positioning the probe on the subject at a location suitable for detecting the subject's blood oxygen level.

Preferably, the probe is positioned such that the oximeter determines the subject's systemic blood oxygen level. The probe location may be chosen from the group consisting of the subject's back (particularly the subject's lower back), head, arm, leg, chest and torso.

It should be noted that the selected (or predetermined) blood oxygen level may comprise a range or a target "setpoint". In fact, multiple predetermined blood oxygen levels may be employed, such that the subject's blood oxygen level is sequentially maintained at multiple selected levels (i.e., interval training). The subject's blood oxygen level may be maintained at each selected level:

(a) for a predetermined period of time;
(b) until the subject has advanced a predetermined distance (e.g., as measured by a GPS system); or
(d) until the subject has performed a predetermined amount of work (e.g., as measured by a GPS system).

Each selected (or predetermined) blood oxygen level may be chosen on the basis of blood oxygen data previously obtained while the subject performed a physical activity. For example, the subject's blood oxygen level at a lactate threshold ("LT") may be determined. Thereafter, each selected blood oxygen level may be chosen on the basis of the subject's LT (e.g., at LT, or a predetermined percentage of LT). Alternatively, each selected level may be chosen on the basis of the duration of the physical activity. For example, the selected blood oxygen level may be higher when the duration of the activity is greater.

In order to facilitate the method of controlling the subject's performance of a physical activity, an alarm may be provided. The alarm may be configured to indicate (i.e., provide an audible and/or visible indicia) when the subject's blood oxygen level is not at the selected level (e.g., outside of a selected range, or not within a certain percentage of a setpoint). A display unit configured for displaying the subject's blood oxygen level may also be provided in order to facilitate performance of the method of controlling. When the subject is a human, the display unit may be configured to display blood oxygen data to the subject or to another (such as a coach or trainer monitoring the subject's performance). For animal subjects, the display unit may be configured to display blood oxygen data to an individual such as a trainer or, in the case of horses and camels, a jockey.

It will be appreciated that the exercise monitoring systems of the present invention may be used for the methods of controlling a subject's performance of a physical activity described herein. In fact, the subject's velocity, pace, workload, and/or distance traveled may be measured by an electronic positioning device provided on the exercise monitoring system.

Still another embodiment of the present invention comprises a method of reducing a subject's blood oxygen level variability while the subject performs a physical activity, comprising:

a. periodically measuring a subject's blood oxygen level while the subject performs a physical activity; and
b. adjusting the manner in which the physical activity is performed in order to reduce blood oxygen level variability.

The time variability of the subject's blood oxygen level may also be indicated (e.g., displayed) to the subject. The time variability of blood oxygen level may be quantified in a variety of manners, such as the standard deviation of the subject's blood oxygen level. The monitoring systems of the present invention may even be configured to activate an alarm when the time variability exceeds a predetermined level.

A method of determining a fitness indicator of a subject is also provided, wherein this method comprises:

(a) recording a subject's blood oxygen level while the subject performs a physical activity;
(b) varying the subject's workload (e.g., periodically increasing workload) while continuing to record the subject's blood oxygen level; and
(c) determining a fitness indicator of the subject on the basis of the recorded blood oxygen data.

The fitness indicator may comprise, for example, the subject's lactate threshold or VO2max (the milliliters of oxygen consumed per kilogram of body weight per minute). The subject's velocity (and optionally altitude) may be measured by a GPS device, such that the subject's workload may then be determined using velocity (and optionally altitude) measurements provided by the GPS device.

A method of stabilizing blood oxygen levels while exercising is also provided, and comprises:

(a) monitoring the level of blood oxygen while exercising;
(b) adjusting breathing while continuing to exercise in order to stabilize the level of blood oxygen.

Another embodiment of the present invention comprises a method of comparing a subject's physical fitness to their physical fitness on a previous occasion, comprising:

(a) measuring an individual's blood oxygen level while the individual performs a physical activity at a predetermined workload, velocity or pace; and
(b) measuring the individual's blood oxygen level on a subsequent occasion while the individual performs the physical activity (particularly at the same predetermined workload, velocity or pace).

For example, if the subject's blood oxygen level (e.g., the subject's average blood oxygen level) is higher on a subsequent occasion, the subject's fitness will have been improved.

DETAILED DESCRIPTION OF THE PREFERRED EMBODIMENTS

The present invention provides an exercise monitoring system, as well as training and analytical methods useful for subjects (both human and animal) performing physical activities. The systems and methods of the present invention, for example, provide real-time data and feedback useful to individuals performing a physical activity (such as athletes). The monitoring system may include an electronic positioning device (such as a GPS device) and/or a physiological monitor (such as an oximeter or a heart rate monitor).

The electronic positioning device uses electromagnetic signals from three or more sources in order to provide data indicative of one or more of the subject's location, altitude, velocity, pace and/or distance traveled. By way of example, the electronic positioning component may comprise a GPS device which utilizes signals from satellites of the Global Positioning System (i.e., "GPS") in order to provide real-time data concerning at least one of the subject's location, altitude, heading, velocity, pace and distance traveled, and may optionally provide a precise time measurement.

The physiological monitor may comprise an oximeter which measures the subject's blood oxygen level, and may also measure the subject's heart rate. Alternatively, the physiological monitor may comprise a heart rate monitor which measures the subject's heart rate.

One embodiment of the monitoring system of the present invention includes both an electronic positioning device and a physiological monitor (such as an oximeter or heart rate monitor) as part of an integrated monitoring system. Such an integrated monitoring system allows velocity, pace, and/or distance traveled information provided by the electronic positioning device to be used in conjunction with data provided by the physiological monitor. In this manner, exercising subjects can monitor, control and/or analyze their performance while exercising at any location (e.g., outside of a laboratory).

The present invention also provides analytical and training methods which utilize data provided by: (a) a physiological monitor; (b) an electronic positioning device (such as a GPS device); or (c) the combination of an electronic positioning device and a physiological monitor (such as a heart rate monitor or an oximeter). It should be pointed out that the various analytical and training methods of the present invention do not require the use of the exercise monitoring systems of the present invention. However, the exercise monitoring systems of the present invention may be configured for implementation of the analytical and training methods described herein.

The monitoring systems, as well as the analytical and training methods, provided by the present invention may be used on both human and animal subjects. Hence, the term "subject" is intended to encompass both humans and animals. By way of example, embodiments of the exercise monitoring systems of the present invention may be used for the testing and/or training of horses and other animals typically involved in racing sports (including dogs and camels). Of course, these methods can also be used in the testing and/or training of other animals not necessarily involved in racing sports (such as rehabilitating an injured animal by putting the injured animal through a training program).

FIG. 1 is a schematic illustration of one embodiment of an exercise monitoring system according to the present invention. The system of FIG. 1 generally comprises an electronic positioning device 5 and a physiological monitor 6, both of which are in electrical communication with a display unit 7. Electronic positioning device 5 is configured to receive electromagnetic signals from three or more sources so that the monitoring system can determine (and display by means of display unit 5) at least one of a subject's location, altitude, heading, velocity, pace, and distance traveled. By way of example, electronic positioning device 5 may be configured to receive electromagnetic signals, and process those signals in order to determine at least one of a subject's location, altitude, heading, velocity, pace, and distance traveled. The determined data may then be transmitted to display unit 7 for display to the subject or other individual monitoring the subject's performance of a physical activity. Similarly, physiological monitor 6 is configured to acquire physiological data from the subject for display by means of display unit 5. By way of example, physiological monitor 6 may be configured to determine one or more physiological indicia (such as the subject's blood oxygen level or heart rate). The determined physiological indicia may then be transmitted to display unit 7 for display to the subject or other individual monitoring the subject's performance of a physical activity.

Figure 2:
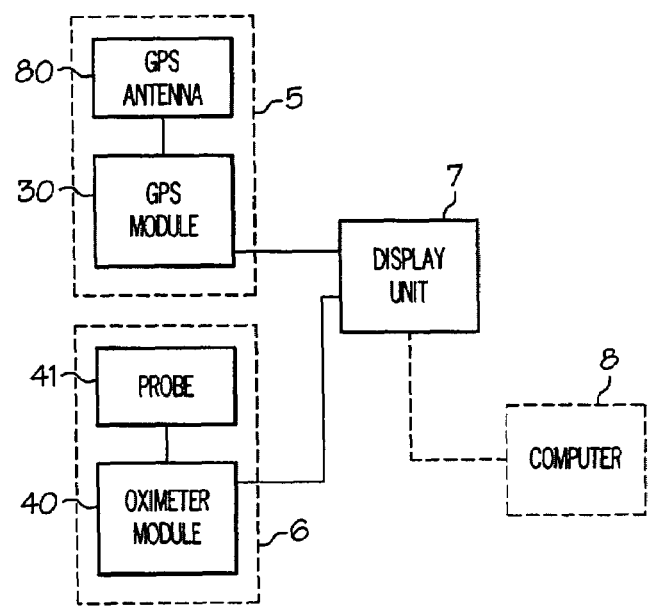
FIG. 2 is a schematic illustration of an exercise monitoring system according to another embodiment of the present invention.

FIG. 2 schematically depicts a more specific embodiment of an exercise monitoring system according to the present invention. In the embodiment of FIG. 2, electronic positioning device 5 comprises a GPS device which includes a GPS antenna 80, and a GPS module 30. Physiological monitor 6 comprises an oximeter which includes a probe 41, and an oximeter module 40. Display unit 7 may comprise any of a variety of structures configured for displaying data. For example, a simple display unit may include a screen which displays the subject's speed (e.g., in miles per hour) and blood oxygen level (e.g., in terms of the percentage of oxygen saturation). The display unit may optionally be configured for linking to (e.g., in electrical communication with) a computer 8 (such as a personal computer of "PC"). Such linking may be provided by a cable, in infrared link, or other means well-known to those skilled in the art. In this manner, data may be stored in computer 8 for later retrieval and analysis.

An exercise monitoring system according to the present invention may comprise a single structure, or may be subdivided into one or more component structures. Thus, one embodiment of the present invention includes a data acquisition component and a separate data display component (i.e., display unit) which are in electrical communication with each other through a wired link (e.g., and electrical cable) or a wireless link (e.g., via radio wave transmission). The data acquisition component may include at least one of an electronic positioning device and a physiological monitor, and may be configured to be worn by a subject performing a physical activity.

A variety of configurations may be provided for the data acquisition component, depending in part upon the nature of the physical activity to be performed as well as the type of data to be acquired. For example, a physiological monitor will often include a sensor or probe which interacts with the subject to acquire physiological data (such as heart rate and/or blood oxygen level). The physiological sensor or probe may be incorporated into the data acquisition component, or may be provided as a separate unit which is in communication with the data acquisition component. For example, the physiological sensor or probe may be remote from the data acquisition component, yet in electrical communication with the data acquisition component over a wired or wireless connection (see, e.g., FIG. 18). When the sensor or probe is incorporated into the data acquisition component itself, the data acquisition component may be configured to ensure proper positioning of the sensor or probe on the subject (i.e., in a position operable to acquire the desired physiological data). Of course, the data acquisition component of a monitoring system according to the present invention may even comprise multiple structures which are physically separate from each other.

The data display component may likewise be provided in a variety of configurations, and its configuration may even be chosen based upon the particular physical activity to be performed. By way of example, the display component may be worn by the subject, worn by another individual, attached to an apparatus associated with the physical activity (e.g., mounted on a bicycle) or provided as a separate, standalone unit.

Figure 3:
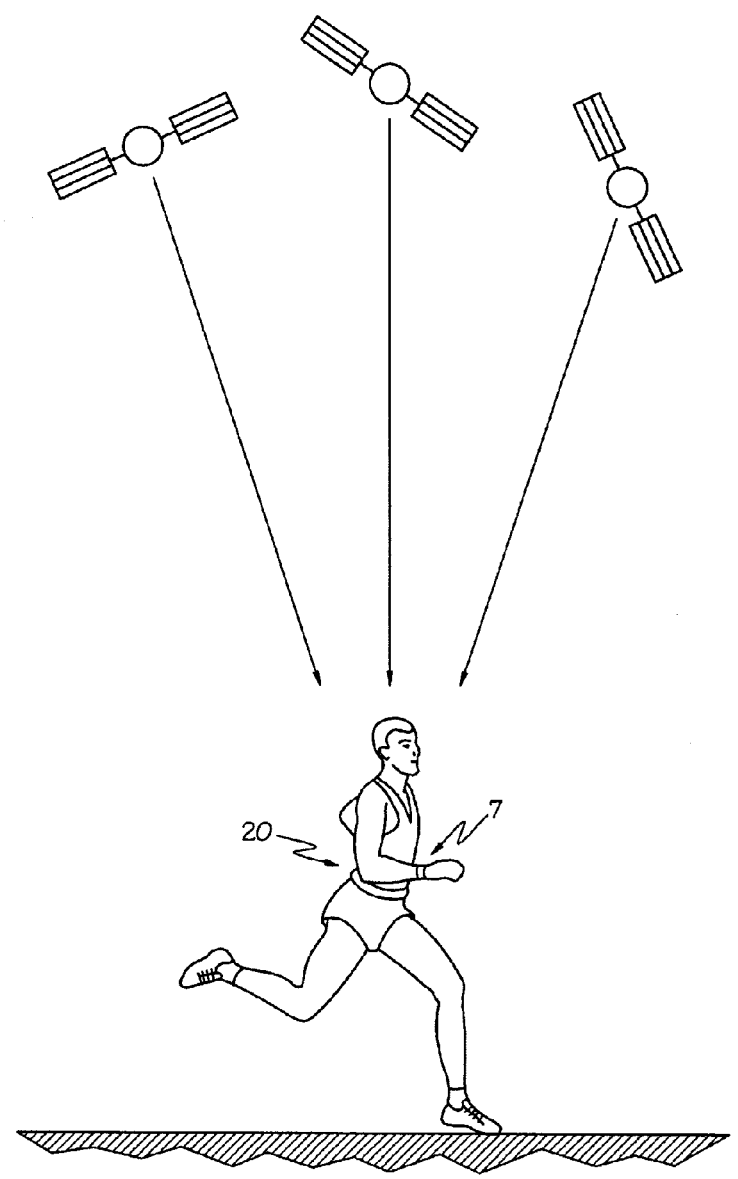
FIG. 3 depicts a human subject performing a physical activity using one embodiment of a monitoring system of the present invention.

FIG. 3 depicts a human subject performing a physical activity, namely running, using a monitoring system according to one embodiment of the present invention. In the monitoring system depicted in FIG. 3, the data acquisition component is depicted at 20, and is worn about the subject's waist. The data display component is depicted at 7, and is worn about the subject's wrist. While the system shown in FIG. 3 provides separate data acquisition and data display components, it will be understood that these two components can be provided in a single structure. In addition, the configuration of data acquisition component 20 and data display component 7 in FIG. 3 is merely exemplary of one embodiment of a monitoring system according to the present invention. The structural features of the specific embodiment of the monitoring system of FIG. 3 will be further described below, after the electronic configuration has been described.

Figure 5:
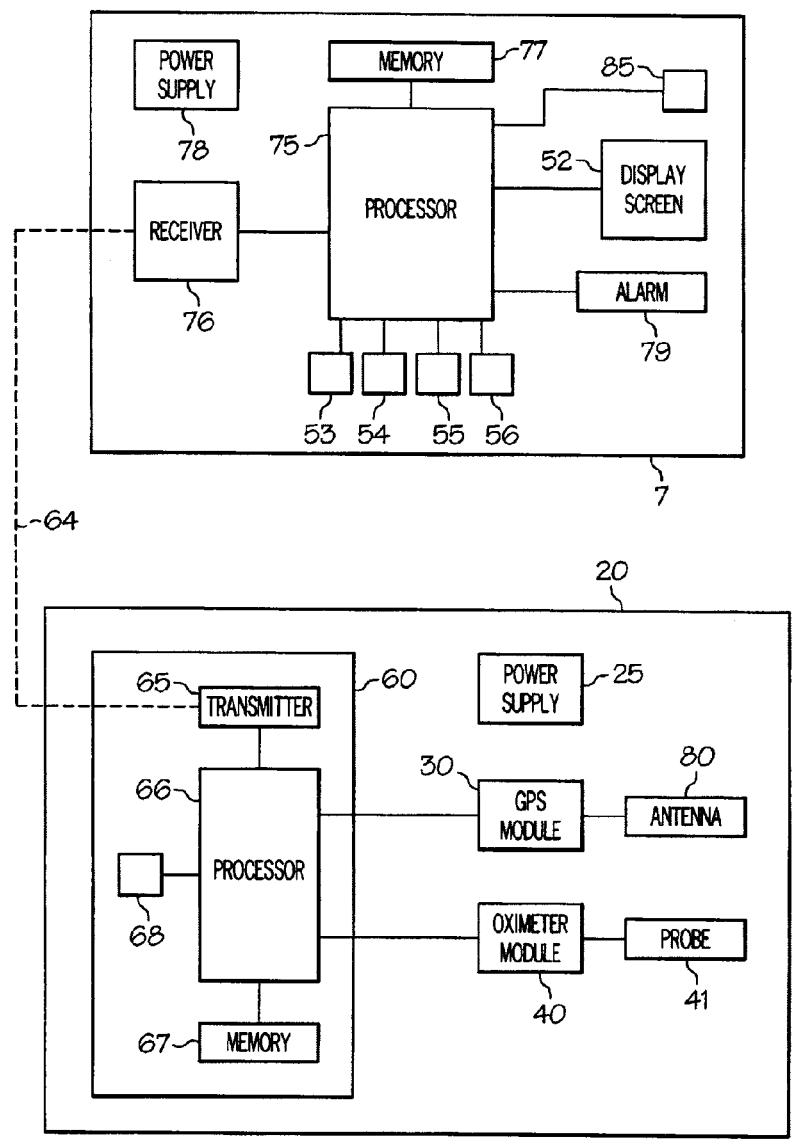
FIG. 5 is a schematic illustration of the monitoring system depicted in FIG. 3.

As mentioned previously, the data acquisition component of the monitoring system of the present invention may include an electronic positioning device and/or a physiological monitor (such as an oximeter or a heart rate monitor). In the schematic illustration of an exemplary monitoring system in FIG. 5, data acquisition component 20 includes both an electronic positioning device and a physiological monitor. In the embodiment of FIG. 5, the electronic positioning device comprises a GPS device which may include a GPS antenna 80 and a GPS processing module 30. As further detailed below, antenna 80 receives GPS satellite signals, and signal output from antenna 80 is processed by GPS processing module 30 in order to provide an electrical signal which includes, for example, data indicative of the user's location. Data from GPS module 30 is provided to processor/transmitter module 60 where it may be further processed and then transmitted to display component 7 over link 64.

It should be noted that the electronic positioning device used in embodiments of the monitoring system of the present invention is not limited to a GPS device. Thus, the term electronic positioning device is intended to be inclusive of devices which receive electromagnetic signals from three or more sources, and thereafter process those signals in order to provide data indicative at least one of the subject's location, altitude, heading, velocity, pace and distance traveled. For example, an electronic positioning device which detects radio wave and/or microwave signals from at least three sources may be used, wherein the received signals are processed in a manner similar to the processing of GPS signals in order to determine the subject's location, altitude, heading, velocity, pace and/or distance traveled. Even signals from cellular phone towers may be employed. In addition, the term "GPS device" is intended to include devices which utilize signals received from satellites of the Global Positioning System developed by the United States Department of Defense, as well as systems which utilize signals received from satellites of the Global Orbiting Navigation Satellite System ("GLONASS") developed by the former Soviet Union (or any other satellite-based positioning system which receives and processes electromagnetic signals from three or more satellites).

Data acquisition component 20 of FIG. 5 also includes a physiological monitor; in this case an oximeter which may include an oximetry probe 41 and an oximeter module 40. Probe 41 acquires data indicative of the subject's blood oxygen level (and optionally heart rate), and oximeter module 40 processes data received from probe 41 in order to provide an electrical signal which includes data indicative of the subject's blood oxygen level (and optionally data indicative of the subject's heart rate). Blood oxygen data from oximeter module 30 is provided to processor/transmitter module 60 where it may be further processed and then transmitted to display component 7 over link 64. Data acquisition component 20 also includes a power supply 25 which provides electrical power to GPS module 30, oximeter module 40, probe 41, and processor/transmitter 60, as needed. GPS antenna 80 may also receive electrical power from power supply 25 when an active GPS antenna is used.

It will be understood that the physiological monitor used in embodiments of the monitoring system of the present invention is not limited to an oximeter. The physiological monitor may alternatively comprise, for example, a heart rate monitor which may include a heart rate module and associated sensor or probe for acquiring data indicative of the subject's heart rate. The data acquired by a heart rate monitor sensor or probe is processed in the heart rate module in order to provide data indicative of the subject's heart rate to processor/transmitter module 60 for further processing and transmittal to display component 7 over link 64.

Processor/transmitter module 60 may include a processor 66 which processes data received from oximeter module 40 and GPS module 30 in accordance with instructions stored in memory 67. The data is thereafter transmitted to display component 7 by a wired or wireless link 64. Thus, electronic link 64 may merely comprise one or more electrical cables or wires located between processor 66 and display component 7 (see. e.g., FIG. 19). Alternatively, data may be transmitted by a wireless link using, for example, radio waves. Thus, in the embodiment of FIG. 5, processor/transmitter module 60 includes an RF transmitter 65 which transmits data received from processor 66 via radio waves to receiver 76 of display component 7.

As mentioned above, display component 7 includes a receiver 76 for receiving data transmitted by data acquisition component 20. The received data may include, for example, data indicative of the subject's location, altitude, heading, velocity, pace, distance traveled, blood oxygen level and/or heart rate, (and optionally the current time as determined by the GPS device). This data is then provided to processor 75 wherein it may be further processed in accordance with instructions stored in memory 77. After processing, acquired and/or calculated data is displayed on display screen 52 where it is visible to the subject or an individual monitoring the subject's performance. Display component 7 may also include a power supply 78 for supplying power to processor 75, receiver 76, and other components, as necessary, within display component 7.

It should be noted that transmitter 65 and receiver 76 may alternatively each comprise transceivers so that electrical signals may be transmitted in both directions (i.e., from data acquisition component 20 to display component 7, and from display component 7 to data acquisition component 20).

Display component 7 may also include one or more alarms 79, each of which provides an audible and/or visual alarm in response to a signal received from processor 75. A plurality of input devices may also be provided on display component 7 so that the subject or other individual may control the processing and/or display of acquired data on display screen 52. Such input devices may comprise, for example, input switches 53–56. Display component 7 may further include a peripheral interface 85 which allows display component 7 to be linked to an external device such that data may be transmitted from display component 7 to the external device (such as a PC, as described previously). In this manner, data concerning the subject's performance of a physical activity may be stored for further processing, analysis and/or retrieval. Peripheral interface 85 may be configured in a variety of manners, depending upon the type of connection to the external device (such as a PC). For example, data may be transmitted from display component 7 to a PC over a wired link. Thus, peripheral interface 85 may merely comprise an electrical terminal to which one end of a cable may be attached. The other end of the cable may then be attached to the PC, such as through a USB port or a serial port. Alternatively, display component 7 may transmit data by means of a wireless link, such as by radio waves or infrared. Thus, peripheral interface 85 may also include a transmitter capable of transmitting radio waves or an infrared signal to a PC which is configured to receive radio waves or an infrared signal. A variety of other structures well-known to those skilled in the art may also be used for peripheral interface 85 in order to transmit data to a PC or other external device.

Electronic Positioning Device

As mentioned above, one embodiment of the monitoring system of the present invention includes an electronic positioning device which determines the subject's location, altitude, heading, velocity, pace, and/or distance traveled based upon electromagnetic signals received from three or more sources. While other positioning devices may be employed, one embodiment of the monitoring system of the present invention employs a GPS device. In general, the GPS device receives electromagnetic signals from three or more satellites, and computes the user's location based upon those signals. In essence, each satellite signal provides the three-dimensional location of the satellite at a precise time. The GPS device then computes the time it took for each signal to reach the GPS device, and this data is then used to compute the user's precise location (typically in terms of the user's longitude and latitude at the time of receiving the GPS satellite signals, and optionally the user's altitude).

The GPS device may generally include an antenna (an active or passive antenna) and a GPS processing module, as previously described. The antenna receives GPS signals from three or more orbiting satellites and transmits the acquired data to the GPS processing module. Thus, as shown in FIG. 5 which is a schematic illustration of one embodiment of the present invention, GPS antenna 80 is in electrical communication with GPS processing module 30, and therefore transmits data acquired from three or more GPS satellites to GPS module 30. It should be noted that while GPS antenna 80 and GPS module 30 are depicted as separate units, they may alternatively be combined into a single structure. GPS processing module 30 then computes the precise location of the subject, and may provide an electrical signal indicative of this position (e.g., in terms of latitude, longitude, and altitude) to processor/transmitter module 60 for further processing.

While GPS processing module 30 may merely transmit raw data indicative of the subject's position to processor/transmitter module 60, GPS module 30 may alternatively process the location data in order to compute, and provide an electrical signal indicative of the subject's velocity, heading, pace and/or distance traveled, as well as the current time. The computed data may then be transmitted to module 60 for further processing and transmittal to display component 7. Of course, it will be understood that, depending upon the level of processing provided by GPS module 30, processor/transmitter module 60 may simply receive data from GPS module 30 and pass the data substantially unaltered to display component 7 via link 64. Thereafter, the transmitted data may be further processed within display component 7, as needed, so as to provide additional data such as average velocity, average pace, workload (based on the subject's weight) and/or other useful information as desired.

in order to compute the distance traveled, a "start point" must be provided to the monitoring system. If the distance traveled is computed by GPS module 30 or processor 66 of processor/transmitter module 60, the subject's location when data acquisition component 20 is first powered up may be selected as the start point for purposes of calculating the distance traveled. Alternatively, an input device may be provided on data acquisition component 20 in order to commence calculation of the subject's distance traveled. If transmitter 65 of processor/transmitter module 60 is replaced by a transceiver, data acquisition component 20 may also receive a start point signal from display component 7. In this manner, the subject may input a start point (such as by pressing a start button or switch) provided on display component 7 in order to commence calculation of the subject's distance traveled. As yet another alternative, the subject's distance traveled may be computed in processor 75 provided in display component 7, thus alleviating the need to provide a start point signal to data acquisition component 20.

In order to provide the above-described functionality, the GPS device utilized in embodiments of the present invention may employ conventional, commercially-available components. As described in U.S. Pat. No. 5,627,548 which is incorporated herein by way of reference, an integrated circuit (IC) may be used in GPS module 30, wherein the IC includes, for example, a low-noise amplifier for boosting signals received from the GPS antenna, a downconvertor for translating the amplified signals to a more suitable frequency, and one or more processors (such as a code-processor and a navigation processor). Numerous manufacturers provide both GPS antennas, as well as GPS "receivers", the latter of which may be incorporated into GPS module 30 of the present invention. Commercially-available GPS receivers generally comprise a circuit board having thereon one or more microprocessor units, one or more custom integrated circuits, software, and other electronic componentry necessary for performing GPS functions. The GPS antenna (also commercially-available) is merely operatively connected to the GPS module (such as by way of a coaxial cable, or other wired or wireless link). A power supply is also operatively connected to the GPS module. The GPS module will then provide (such as through a suitable electronic connector) an electrical signal which includes data indicative of, for example, the subject's latitude, longitude, altitude, velocity and/or heading, as well the current time (the latter based upon the received satellite signals). Therefore, GPS module 30 may simply comprise a commercially-available GPS receiver, along with suitable connection elements which allow GPS antenna 80, power supply 25, and processor/transmitter module 60 to be operatively connected to the GPS receiver portion of GPS module 30.

One commercially-available GPS receiver which may be used in an embodiment of the present invention is the GPS-PS1 receiver available from p-blox AG, of Zurich, Switzerland. Alternatively, the GPS-MS1 receiver (also available from p-blox AG) may be used. Suitable GPS antennas are also available from p-blox AG, as well as other sources.

While some commercially-available GPS systems simply display the user's location (typically in terms of longitude and latitude values, and optionally altitude), as mentioned previously, an embodiment of the present invention utilizes GPS location data for computing velocity, pace and/or distance traveled. Thus, the GPS device used in embodiments of the present invention may acquire location information at predetermined intervals, such as between about 0.1 and about 1.0 seconds. In this manner, the GPS device is capable of periodically determining the subject's location (e.g., determining the subject's location between about every tenth of a second and about every second). Such periodic location data can then be further processed (such as in the GPS module, or alternatively in processor/transmitter module 60, or even in processor 75 of display component 7) in order to compute the subject's velocity (e.g., speed in miles per hour), pace (e.g., the user's speed in terms of the number of minutes to complete one mile), or distance traveled (e.g., the distance that the user has traveled since an initial start point). The commercially-available GPS receivers mentioned above are generally configured for computing velocity, and may be readily programmed to compute pace and/or distance traveled. In this manner, these commercially-available GPS receivers may be incorporated into GPS module 30 such that GPS module 30 will provide a signal which includes data indicative of the subject's latitude, longitude, altitude, velocity, heading, pace and/or distance traveled (as well as the current time).

An embodiment of the monitoring system of the present invention which includes an electronic positioning device is useful even without the inclusion of a physiological monitor. For example, an individual can use the GPS device of the monitoring system while running (or performing any other physical activity) in order to determine their velocity at any given moment (e.g., in miles per hour), their pace at any given moment (e.g., in terms of minutes per mile), and/or the total distance they have run since an initial start time (e.g., from the moment they begin running).

When the monitoring system includes both an electronic positioning device (such as a GPS device) and a physiological monitor (such as an oximeter or heart rate monitor), data provided by the GPS system may be used in conjunction with the physiological data for performance monitoring, testing and/or training. By way of example, a heart rate monitor device incorporated into a monitoring system according to the present invention may display a subject's heart rate at any given moment, while a GPS device of the system simultaneously displays the subject's velocity and/or pace. In this manner, the subject (or another individual such as a coach or trainer) can more effectively monitor the subject's performance, exertion level and/or progress. By itself, a runner's velocity (or pace) is a poor indicator of performance and/or progress (i.e., improvement). Likewise, heart rate alone is a poor indicator of performance and/or progress when the subject's velocity (or pace) is not known. Simultaneously monitoring velocity (or pace) and heart rate (and/or blood oxygen level), however, provides the missing link; i.e., the physiological effect of running at a certain speed. Thus, incorporating an electronic positioning device and a physiological monitor into an integrated system provides more meaningful data.

Oximeter

As blood is pumped through the lungs, deoxyhemoglobin in the bloodstream absorbs oxygen to become oxyhemoglobin. Thereafter, the oxygenated blood is delivered throughout the body, where the oxygen is released in order to support metabolic function. Medical personnel often monitor a patient's blood oxygen level as one indicator of the patient's overall condition. For example, a patient's blood oxygen level is typically monitored during surgery in order to ensure that sufficient oxygen is reaching the patient's brain and other vital organs.

Blood oxygen levels are typically monitored in terms of the oxygen saturation level, which is defined as the amount of oxyhemoglobin as a percentage of the total hemoglobin. For example, the typical oxygen saturation level of a healthy adult at rest is between about 96% and about 98%, which simply means that between about 96% and about 98% of the hemoglobin in the arterial blood is oxygenated (i.e., converted to oxyhemoglobin). As used herein, the term oximeter includes any device capable of determining blood oxygen level.

Many commercially-available oximeters employ light absorption measurements to determine blood oxygen levels, as well as heart rate. When light is directed towards a volume of blood (such blood in an artery), a portion of the light is absorbed by surrounding tissue as well as the blood. A sensor may then detect the amount of light which is transmitted through or reflected by the blood and surrounding tissue (i.e., light which is not absorbed by the blood or surrounding tissue). During systole, the volume of blood in the artery is increased, and more light will be absorbed by the blood. During diastole, the volume of blood in the artery decreases, and in turn the amount of light absorption decreases. Since light absorption by the surrounding tissue remains constant, the amount of light absorption will vary as a function of heart rate. Therefore, the subject's heart rate can be readily determined simply by monitoring the amount of light absorption (e.g., by measuring the length of time between peak levels of light absorption).

Oxyhemoglobin and deoxyhemoglobin differ in their absorption of light, and these differences in light absorption properties can be employed to determine the blood oxygen level. By measuring light absorption at two or more different wavelengths, blood oxygen level can be readily determined. For example, deoxyhemoglobin absorbs more red light than does oxyhemoglobin, while oxyhemoglobin absorbs more infrared light than deoxyhemoglobin. Since the absorption properties of oxyhemoglobin and deoxyhemoglobin are well-known, the ratio of oxyhemoglobin to total hemoglobin can be readily determined merely by measuring light absorption at a red wavelength and at an infrared wavelength. The ratio of light absorption at the two frequencies (e.g., red light absorption divided by infrared light absorption) can be compared to values in a look-up table in order to provide a measurement of blood oxygen level.

Typically, an oximeter directs light of two different predetermined wavelengths in alternating fashion towards a volume of blood, and a light sensor detects light which is transmitted through or reflected by the blood. Data acquired by the light sensor is then processed in order to provide a measure of the oxygen level of the blood. In the embodiment depicted schematically in FIG. 5, a probe 41 may include a pair of light sources for directing light of two different wavelengths at a volume of blood, as well as a light sensor for detecting light which is transmitted through or reflected by the blood. By way of example, the light sources (such as LED's) may be configured to emit red light (e.g., a wavelength of between about 610 nm and about 650 nm) and infrared light (e.g., a wavelength of between about 810 nm and about 850 nm). Probe 41 is in electronic communication with oximeter module 40 via a wired or wireless connection, such that probe 41 transmits data indicative of detected light to module 40. Oximeter module 40 includes a processor and other electronic componentry which provides an electrical signal indicative of the subject's blood oxygen level, and optionally the subject's heart rate. Oximeter module 40 is in electrical communication with processor/transmitter module 60, such that the electrical signal indicative of the subject's blood oxygen level (and optionally heart rate) is transmitted to processor 66. After processing, processor/transmitter module 60 may transmit the resulting oximetry data to display component 7, as previously described. Alternatively, the oximetry data from oximeter module 40 may be merely transmitted to display component 7 by processor/transmitter module 60.

The oximeter device utilized in embodiments of the present invention may employ commercially-available components in order to provide the functionality described above. For example, numerous manufacturers provide both oximeter probes, as well as oximeter modules which may be used in the present invention. Commercially-available oximeter modules are provided, for example, as integrated circuits which may include one or more microprocessors, software, and other electronic componentry for generating an electrical signal which includes data indicative of the subject's blood oxygen level and heart rate. The oximeter probe (also commercially-available) is merely operatively connected to the oximeter module (such as by way of a wired or wireless connection), and the oximeter module will then provide an electrical signal which includes data indicative of the subject's blood oxygen level and heart rate. A commercially-available oximeter module may be repackaged into an enclosed unit suitable for attachment to a support member (such as a belt to be worn by the subject) in electrical communication with the other elements of data acquisition component 20. One commercially-available oximeter module which may be used in an embodiment of the present invention is the OEM2 Pulse Oximeter Module available from Nonin Medical, Inc. of Plymouth, Minn. Suitable oximeter probes are also available from Nonin Medical, Inc., as well as other sources.

It should be noted that the monitoring systems of the present invention preferably determine, and the analytical and training methods preferably utilize, the subject's systemic blood oxygen level, rather than localized oxygen levels (such as in or near active muscle tissue). When a subject performs a physical activity, particularly a strenuous activity, blood oxygen level within and around working muscles may vary considerably from the subject's systemic blood oxygen level (i.e., the level of oxygen in the bloodstream as a whole). Thus, the monitoring systems according to the present invention are preferably configured in order to minimize any localized variance in blood oxygen levels as compared to the subject's systemic blood oxygen level. This may be accomplished, for example, by positioning the oximetry probe in a location of minimal muscle activity, thereby avoiding active muscle tissues or regions.

Heart Rate Monitor

As mentioned previously, the physiological monitor used in certain embodiments of the present invention may comprise a heart rate monitoring device which provides data indicative of the subject's heart rate. By way of example, oximeter module 40 in FIG. 5 may merely be replaced by a heart rate module which processes data received from probe 41 in order to provide an electrical signal which includes data indicative of the subject's heart rate. In fact, a heart rate module similar in configuration to oximeter module 40 may be employed, except that the electronic componentry need not be configured for determining the subject's blood oxygen level. In addition, probe 41 may be used with a heart rate module, since, as described previously, the light absorption of blood will vary with the subject's heart rate. During systole, the volume of blood in an artery increases, thereby resulting in a detectable increase in light absorption. Thus, the subject's heart rate may be readily determined, for example, by measuring the period of time between light absorption peaks (i.e., peaks corresponding to systole). It should be pointed out, however, that light of a single wave length is sufficient for monitoring the subject's heart rate. Therefore, only a single light source is required in probe 41 if oximeter module 40 is replaced by a heart rate module.

As an alternative to employing light absorption measurements for determining heart rate, electrocardiography ("ECG") may be employed. A beating heart produces electrical pulses which can be readily measured in a variety of manners well-known to those skilled in the art. For example, a pair or electrodes may be positioned against the subject's chest in the region surrounding the heart, such that the electrodes will detect ECG signals. Thus, probe 41 may be replaced by an ECG-type probe having a pair of electrodes suitable for detecting ECG signals and transmitting data indicative of the subject's heart rate to a heart rate module. By way of example, U.S. Pat. No. 5,491,474, which is incorporated herein by way of reference, discloses a telemetric transmitter unit which may be used as a heart rate sensor or probe in embodiments of the present invention. The telemetric transmitter unit of this patent is configured to be worn about the subject's chest such that the electrodes of the transmitter unit are operatively positioned so as to detect ECG signals. As described in U.S. Pat. No. 5,840,039, which is also incorporated herein by way of reference, data indicative of the subject's heart rate may be transmitted by the telemetric transmitter unit to a telemetric receiver unit. In the present invention, the telemetric receiver unit may simply comprise the heart rate module provided by data acquisition units 20. Alternatively, data from the telemetric transmitter unit may be transmitted directly to data display component 7 of the present invention, such as by the methods of U.S. Pat. No. 5,840,039. The transmitted heart rate data may then be further processed by data display component 7, as desired. Of course, it is also contemplated that instead of the wireless data transmission described in U.S. Pat. No. 5,840,039, the heart rate probe or sensor (such as the telemetric transmitter unit described previously) may be in electrical communication with either data acquisition component 20 or data display component 7 by means of one or more wires.

Data Display Component

As mentioned above, display component 7 receives an electrical signal from data acquisition component 20 via a wired or wireless link 64 (see FIG. 5). This electrical signal will generally include data indicative of one or more of the following: location, altitude, velocity, pace, distance traveled, heading, blood oxygen level and heart rate. The electrical signal may be received, for example, by receiver 76 (which may alternatively comprise a transceiver). The received electrical signal is then provided to processor 75 where the data may be further processed in accordance with instructions stored in memory 77. The acquired data may be processed in processor 75 in a variety of manners, depending upon, for example, the type of data which the subject or other individual wishes to monitor. After processing, the data may then be displayed on display screen 52. The subject, or other individual monitoring the subject's performance, may even select the type of data to be displayed by, for example, employing switches 53–56. By way of example, the subject may select one or more predetermined formats for data display utilizing input switches 53–56.

Data display component 7 may also include one or more alarms 79 which provide an audible and/or visible indication to the subject or other individual monitoring the subject's performance. Data display component 7 may be programmed such that an alarm 79 will be activated if a data value departs from a predetermined limit or range. For example, the monitoring system of the present invention may be programmed such that an alarm 79 will be activated if the subject's velocity, pace, distance traveled, blood oxygen level or heart rate is outside a predetermined range. In one embodiment, the subject may program the monitoring system of the present invention, such as by using input switches 53–56, in order to set predetermined levels or ranges for a variety of acquired data. For example, the subject can input an alarm level or range for blood oxygen level, such that an alarm 79 will be activated if the subject's blood oxygen level falls below the predetermined level or outside of the predetermined range. Similar alarm set points can be established by the subject or another individual monitoring the subject's performance for velocity, pace, distance traveled and/or heart rate. In this manner, the subject's performance of the physical activity can be precisely controlled. It should be pointed out that alarms 79 may take a variety of configurations, such as a device capable of generating an audible sound (such as a tone or beep) in response to a signal received from processor 75, or a device capable of generating a visible signal (e.g., a blinking light source) in response to a signal received from processor 75.

As further discussed below, data display component 7 may also include one or more status indicators 57 and 58 (see FIG. 10). Status indicators 57 and 58 may be operatively connected to processor 75 such that one of said status indicators is activated when data acquisition component 20 is not operating properly. For example, the status indicators may merely comprise a portion of display screen 52 which illuminates in order to alert the subject or other individual monitoring the subject's performance that, for example, the GPS device has not acquired the necessary satellite signals, or the physiological monitor is not properly acquiring physiological data from the subject.

Exemplary Embodiment of Exercise Monitoring System

As mentioned previously, FIG. 3 depicts a runner using an exemplary exercise monitoring system according to one embodiment of the present invention. In the monitoring system of FIG. 3, data acquisition component 20 is configured to be worn about the waist of the subject. As more fully described herein, the data acquisition component can comprise any of a variety of structures and configurations, and the structure shown in FIG. 3 is merely exemplary of one embodiment of the present invention. The data display component in FIG. 3 comprises a data display component 7 worn about the wrist of the subject. Once again, as more fully described herein, the data display component can comprise any of a variety of structures and configurations, and that shown in FIG. 3 is merely exemplary of one embodiment.

Data acquisition component 20 acquires data while a subject wearing component 20 performs a physical activity. The acquired data is processed and then displayed by data display component 7. In this manner, data may be acquired while the subject performs the physical activity at any location, thus allowing performance testing and monitoring to be performed anywhere. As shown in the perspective view of FIG. 4, data acquisition component 20 includes a support member 15 which generally comprises an elongate member sized and configured to be worn about the user's waist. Support member 15 may be made from any of a variety of suitable materials, particularly flexible materials such as polyurethane or other plastics which can be manufactured to be both flexible and soft. Support member 15 may include connector elements at each end thereof in order to facilitate securing support member 15 about the user's waist. These connector elements may comprise any conventional elements used to secure a belt about a person's waist, including conventional belt buckle elements, or hook and loop fastener elements. In the embodiment shown, male and female connector elements 21 and 22, respectively, are provided at opposite ends of support member 15. Connector elements 21 and 22 are made from a resilient plastic, thereby allowing male element 21 to be releasably snapped into female element 22 in order to secure support member 15 about the user's waist. Support member 15 may also be adjustable in length to accommodate different waist sizes, and to allow support member 15 to be adjusted for comfort.

Figure 4:
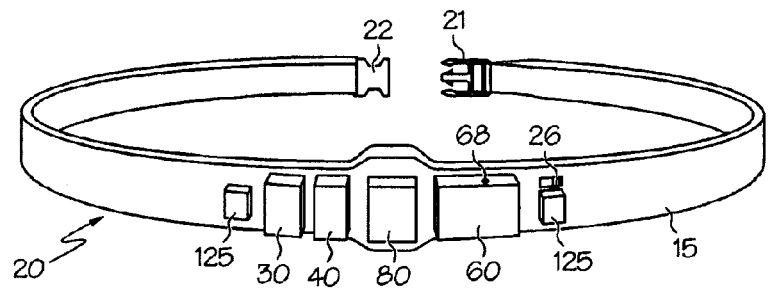
FIG. 4 is perspective view of the data acquisition component of the monitoring system depicted in FIG. 3.
Figure 6:
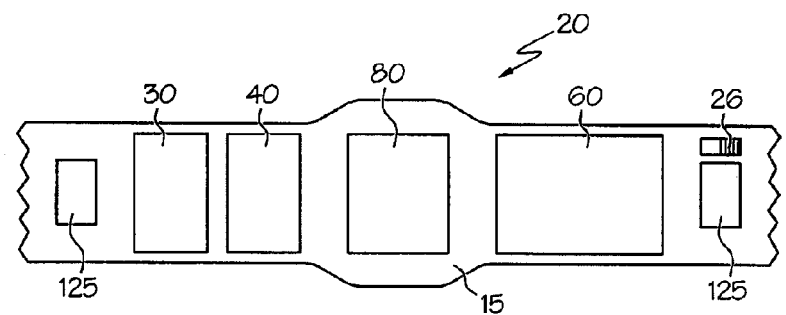
FIG. 6 is an enlarged plan view of a portion of the data acquisition component of the monitoring system depicted in FIG. 3.

As best seen in the enlarged view of FIG. 6, the various modules described previously are mounted on support member 15 in order to provide the desired data acquisition functions. The modules are preferably provided on support member 15 at a side opposite to connector elements 21 and 22 (as shown in FIG. 4). In this manner, support member 15 may be worn about a subject's waist, with connector elements 21 and 22 located in front, with the modules positioned adjacent the subject's lower back. Not only does this arrangement provide for ease of use (i.e., connecting and disconnecting connector elements 21 and 22), it also provides a more comfortable arrangement due to the increased bulk of the modules. In addition, when a probe or sensor (such as an oximeter probe) is incorporated into support member 15, the probe or sensor may be operatively positioned against the subject's lower back. Of course other arrangements may be provided, particularly whenever it is necessary to orient a probe or sensor at some other location with respect to the subject's body.

GPS module 30, oximetry module 40, antenna 80 and processor/transmitter module 60 may be provided on support member 15. Each may be removably attached to support member 15 such that they may removed and attached as needed, or even replaced by other modules which provide different functionality (such as a heart rate monitor module). Each module generally includes electronic circuitry suitable for performing the desired data acquisition and/or processing function, as described above (e.g., acquiring data indicative of blood oxygen level of a subject wearing support member 15).

While each module may include the necessary circuitry for independently acquiring, processing and transmitting data, the embodiment of data acquisition component 20 depicted in FIG. 4 includes circuitry which allows data and other electrical signals to be passed from one module to another. In this manner, for example, a single processor/transmitter module 60 may be employed for not only processing data from GPS module 30 and oximeter module 40, but also for transmitting such data to display component 7. In addition, one or more power supplies, such as batteries 125, may provide power to multiple modules provided on support member 15. In order to provide such electrical integration of data acquisition component 20 and the various modules attached thereto, support member 15 may include a plurality of electrical conduits to allow electrical signals to be exchanged between the various modules, as desired. Each of the modules (including antenna 80) is configured such that each may be attached to belt 20 in electrical communication with one or more of the electrical conduits of belt 20.

Figure 12:
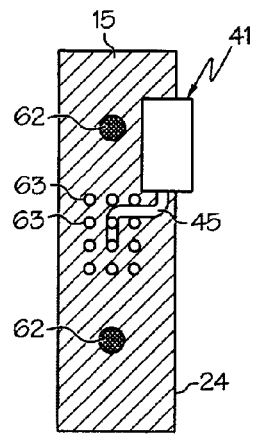
FIG. 12 is a cross-sectional view of the data acquisition component of FIG. 7, taken along the line 12—12 thereof.

Electrical conduits may be provided on support member 15 in a variety of manners, such as along inner surface 24 or outer surface 23 of support member 15. Alternatively, a plurality of electrical conduits may be provided within the interior of support member 15. As best seen in the cross-sectional view of FIG. 12, a plurality of electrical conduits 63 extend through the interior of support member 15, and are thus protected and insulated by the material from which support member 15 is formed. Individual conduits may be provided within support member 15 (as shown in FIG. 12), or a flexible electrical strip such as a membrane circuit may be provided within support member 15. One or more separate conduits for transmitting electrical power may also be provided in support member 15. Thus, as seen in FIG. 12, first and second power cables 61 and 62, respectively, extend through the interior of support member 15. Electrical conduits 63 and power cables 61 and 62 may extend through the interior of support member 15 in any of a variety of patterns; generally as necessary to provide the desired electrical connections between the various modules and power supplies. Of course, it will be understood that conduits for transmitting electrical power from batteries 25 to the various modules may also be provided on a flexible electrical strip along with the electrical conduits described previously.

The various modules and support member 15 are configured such that each module may be attached to support member 15 in electrical communication with one or more of electrical conduits 63, and optionally one or both of power cables 61 and 62. As best seen in the top plan view of FIG. 7, wherein the modules have been removed from support member 15, a plurality of electrical apertures 29 (also commonly referred to as female connectors or female electrical terminals) are provided on support member 15. Electrical apertures 29 may be arranged in any desired pattern, and the rectangular grid shown is merely exemplary of one possible arrangement. The arrangement of electrical apertures 29, however, should correspond with the arrangement of electrical connectors provided on each module (as described below). Each aperture 29 is in electrical communication with one of electrical conduits 63. A pair of power apertures 28 are also provided above and below each grid of electrical apertures 28, and each power apertures is in electrical communication with one of first and second power cables 61 and 62.

Figure 7:
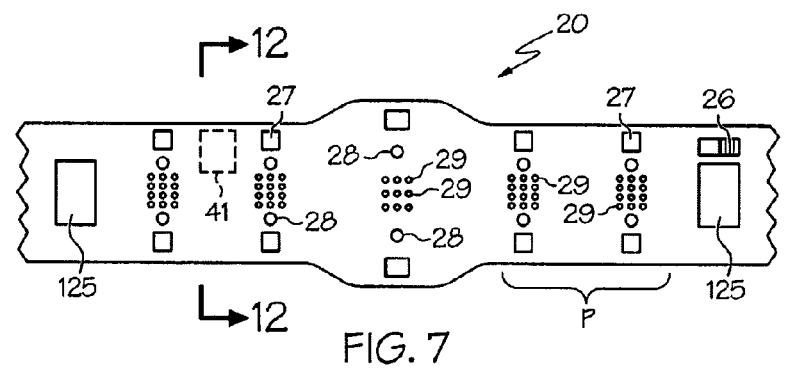
FIG. 7 is a view similar to FIG. 6, wherein the modules have been removed from the support member of the data acquisition component.
Figure 8:
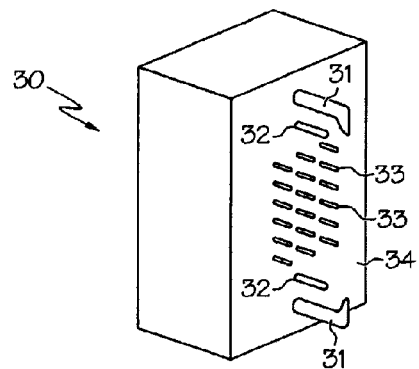
FIG. 8 is a perspective view of an oximeter module of the data acquisition component of the monitoring system depicted in FIG. 3.

Turning to FIG. 8 which depicts GPS module 30, a plurality of electrical connectors 33 (also commonly referred to as male connectors or male electrical terminals) extend away from rear surface 34 of GPS module 30. Electrical connectors 33 may be arranged in the same pattern as electrical apertures 29 on support member 15. Similarly, GPS module 30 includes a pair of power connectors 32 which extend away from rear surface 34 of module 30, above and below the grid of electrical connectors 33. In this manner, GPS module 30 may be attached to support member 15, with each electrical connector 33 engaging an electrical aperture 29 on support member 15 and each power connector 32 engaging a power aperture 28 on support member 15. Thus, the arrangement of electrical connectors 33 and power connectors 32 on GPS module 30 should correspond to an arrangement of electrical apertures 29 and power apertures 28 on support member 15. In the embodiment of FIG. 7, each rectangular grid of electrical apertures 28 and corresponding pair of power apertures 28 (i.e., above and below the rectangular grid) are identical. Thus, GPS module 30 can be attached to support member 15 at a variety of locations. The other modules may have an arrangement of electrical connectors 33 and power connectors 32 which is similar to that for GPS module 30 (as shown in FIG. 8). In this manner, each module can be attached to support member 15 at a variety of locations. Alternatively, each module may have a unique configuration which allows that module to be attached to support member 15 only at one or more selected locations.

In order to further secure GPS module 30 to support member 15, a pair of mounting tabs 31 may also extend away from rear surface 34 of module 30. A pair of corresponding mounting apertures 27 are provided on support member 15. Mounting tabs 31 and mounting apertures 27 are arranged such that GPS module 30 may be attached to support member 15 with each mounting tab 31 engaging a mounting aperture 27 on support member 15. Each mounting tab 31 may be resilient in nature such that the end portion of the mounting tab will engage a mounting aperture, thereby securely attaching GPS module 30 to support member 15. The other modules may each include similar mounting tabs such each module may be securely attached to support member 15 in the same manner. In fact, each module may have a shape and configuration similar (or even identical to) GPS module 30. Of course a variety of alternate configurations may be employed for each module, particularly if the system is designed such that each module can be attached to support member 15 only at a single, predetermined location. It should be pointed out that processor/transmitter module 60 of the embodiment shown in FIG. 4 is sized somewhat larger than GPS module 30 and oximeter module 40. Thus, module 60 may include four mounting tabs 31 for attachment to support member 15 at region P shown in FIG. 7.

While individual power supplies may be provided in each module, one or more power supplies may be provided on support member 15 in order to provide electrical power to each module. A variety of sources of electrical power may be provided, such as rechargeable or non-rechargeable batteries, one or more solar cells, or a combination of any of the foregoing power sources. In the embodiment shown in FIG. 4, a pair of batteries 125 are provided on support member 15 in electrical communication with first and second power cables 61 and 62. Each battery 125 may be removably or permanently secured to support member 15, and may be located internally or externally of support member 15. Each battery 125 may provide power to selected modules, or both batteries may be configured to provide power to all of the modules. A power switch 26 may also be provided on support member 15. Power switch 26 is operable for turning support member 15 on and off (i.e., allowing power to be supplied to the modules when switch 26 is in its on position).

Figure 15:
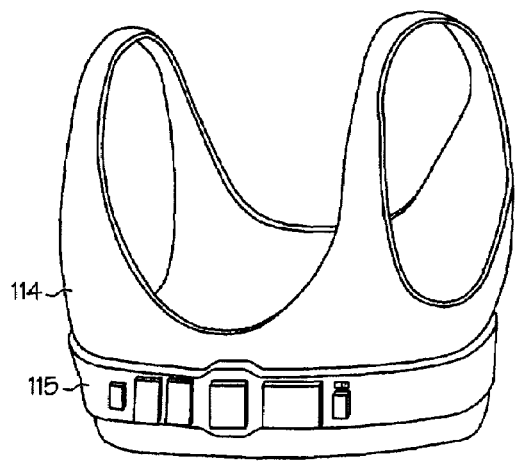
FIG. 15 is a perspective view of an alternative embodiment of a data acquisition component according to the present invention, wherein the data acquisition component is configured to be worn about the chest of a human subject.

FIG. 15 depicts an alternative data acquisition component according to an embodiment of the present invention. In the embodiment of FIG. 15, the data acquisition component is configured similar to a bra, and therefore includes a fabric article 114 configured to be worn about a subject's chest. A support member 115 is incorporated into the fabric article. In fact, support member 115 may be configured identical to support member 15 described above, and includes the various modules and other components described in conjunction with the data acquisition component of FIG. 4. Support member 115 may be secured to fabric article 114 in a variety of manners, such as an adhesive or by sewing support member 115 directly to fabric article 114. An opening may also be provided in fabric article 114 in the region of the oximeter probe in order to allow the probe to be urged against the subject's back, such as below the subject's shoulder blade. Of course it will be recognized that support member 115 may be used without fabric article 114, such that support member 115 is merely secured about the subject's chest similar to the manner in which the telemetric transmitter unit of a conventional heart rate monitor is secured about a user's chest.

Figure 11:
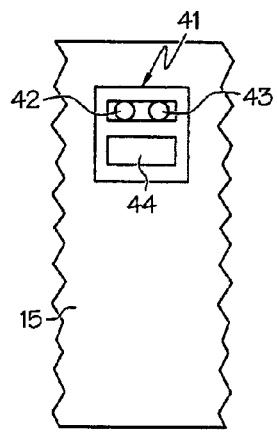
FIG. 11 is a rear plan view of a portion of the data acquisition component of FIG. 7.

As best seen in FIGS. 11 and 12, probe 41 is integrally provided on support member 15 such that probe 41 extends partially away from inner surface 24 of support member 15. In this manner, support member 15 will urge probe 41 against the subject's skin in the lower back region in order to acquire blood oxygen data. An electrical connector 45 (such as a cable or wire) electrically connects probe 41 to the oximeter module. Probe 41 includes a first light source 42 configured for emitting red visible light, and a second light source 43 configured for emitting infrared light. First and second light sources 42 and 43 may comprise, for example, LED's. Probe 41 also includes a light sensor 44. Thus, probe 41 may acquire blood oxygen and heart rate data in the manner described previously.

Figure 18:
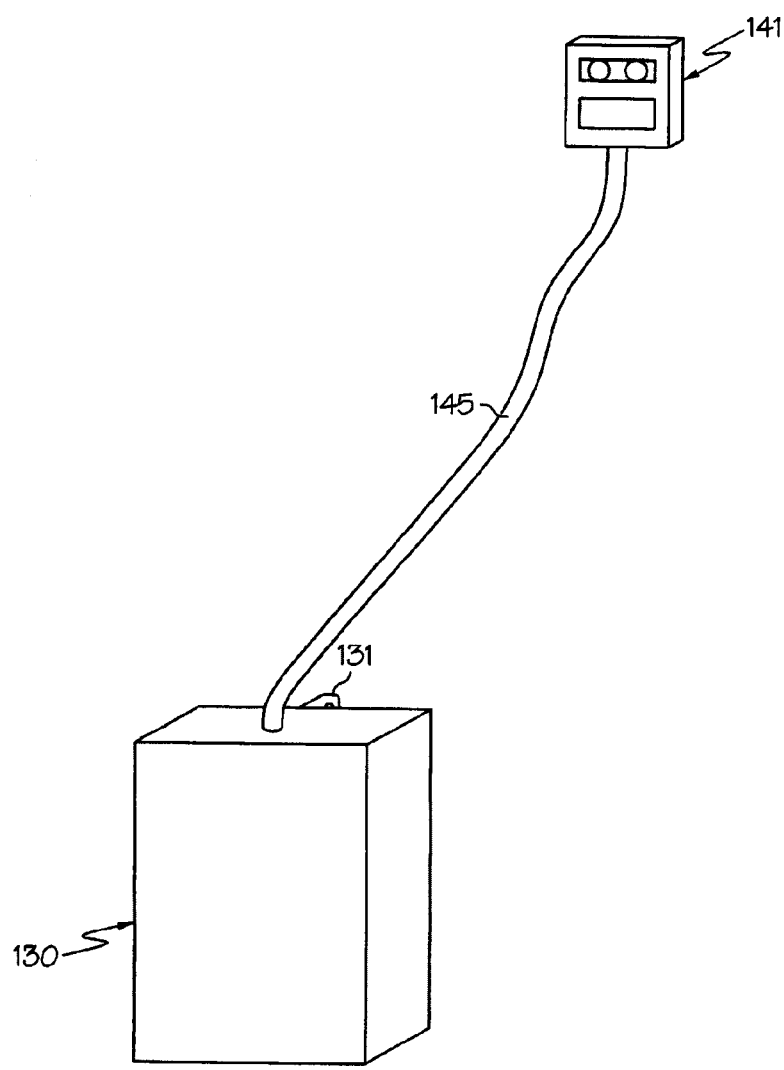
FIG. 18 is a perspective view of an alternative embodiment of an oximeter used in a monitoring system according the present invention.

FIG. 18 depicts an alternative embodiment of a physiological monitor for use with the data acquisition component of the monitoring system of the present invention. In the embodiment of FIG. 18, probe 141 is remote from the support member for the data acquisition component of the monitoring system. Thus, probe 141 is operatively connected to oximeter module 130 by means of a cable 145. Of course another suitable wired or wireless link may be used in place of cable 145. The configuration of FIG. 18 is advantageous in that probe 141 may be attached to the subject in a variety of locations, such as the subject's lower back, torso, beneath the shoulder blade, or even on the subject's head (such as on the subject's forehead). Therefore, probe 141 may be positioned in a variety of locations. The embodiment of FIG. 18 is also advantageous when the monitoring system is used on a non-human subject such as a horse. Probe 141 may be attached to the horse's forehead (such as using adhesive or a suitable harness), while a jockey or trainer riding the horse wears data acquisition component 20 (such as around their waist).

Display Component

As discussed previously, particularly in conjunction with the description of the schematic illustration of FIG. 5, the monitoring system of the present invention includes a display component (or display unit) for displaying data which has been acquired and processed by the data acquisition component. The display component of the monitoring system of the present invention may comprise any of a variety of structures suitable for displaying data and other information to the subject or an individual monitoring the subject's physical activity (such as a trainer or a coach). The display component may therefore comprise a personal computer having a monitor associated therewith, wherein the personal computer receives data from the data acquisition component via a wired or wireless connection. Alternatively, the display component may comprise a display device which is configured for use in a particular physical activity, such as a display unit which attaches to a bicycle in a location visible to the rider (e.g. a handlebar-mounted display unit).

Figure 19:
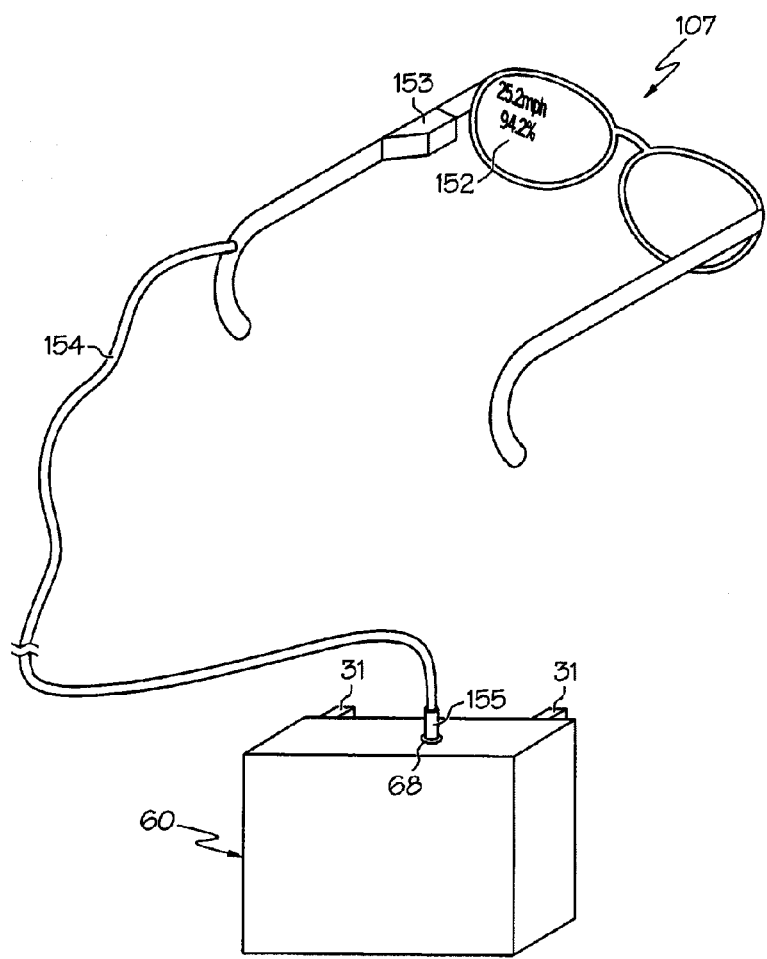
FIG. 19 depicts an alternative display unit of a monitoring system according to the present invention.

The display component may alternatively comprise a "heads-up" type display unit configured for displaying data and other information directly to the subject. As used herein, the term "heads-up display unit" refers to any display device which is configured to display data to the subject in front of the subject's face. Such a device may be configured to project data and other information onto glasses worn by the subject, swimming goggles, a visor worn by the subject (such as a visor attached to a bicycle helmet), or even onto a display screen which is physically attached to helmet, visor, hat or other structure positioned on the subject's head in a position so that data and other information displayed thereon is directly visible to the subject. FIG. 19 depicts an exemplary heads-up display unit 107 comprising glasses of the type described in patent application number WO 99/23524 (which is incorporated herein by way of reference). Such glasses include a display assembly 153 which displays data onto eyeglass lens 152. A cable (or wire) 154 connects the glasses to processor/transmitter module 60, through peripheral interface 68 provided on module 60. Such a display device is available from the MicroOptical Corporation of Boston, Mass. Alternatively, the display device described in patent application number WO 99/23525 (which is incorporated herein by way of reference) may be used. The display device described in this latter patent application essentially provides a display screen positioned in front of the subject's eyeglasses (or is otherwise positioned in front of the subject's face) so that the subject may view data and other information provided on the display screen while still being able to see through the glasses. The focal point of the display screen, however, may be adjusted so as to appear several feet in front of the subject's glasses. In this manner, the subject may view the data and other information provided on the display screen, while still being able to use the glasses in a normal fashion. Other suitable heads-up type display devices are well-known to those skilled in the art, and may be utilized in the monitoring system of the present invention.

Figure 9:
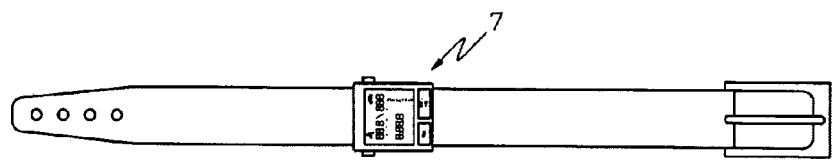
FIG. 9 is a top plan view of the display component of the exercise monitoring system depicted in FIG. 3.
Figure 10:
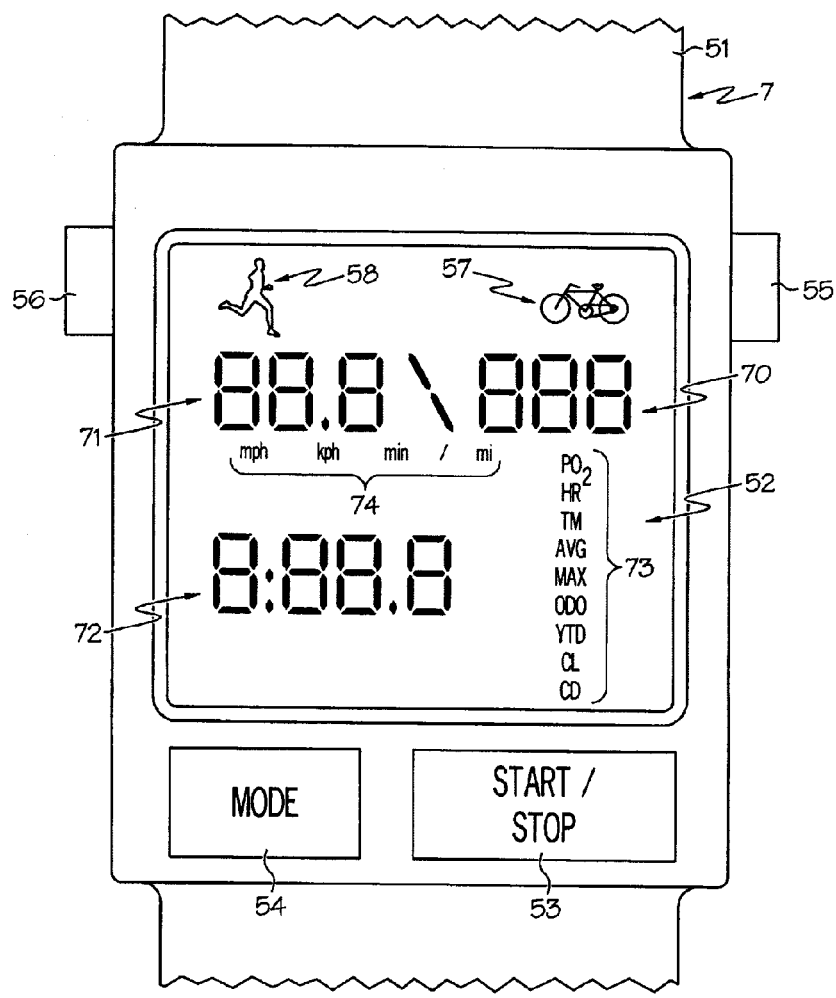
FIG. 10 is an enlarged top plan view of a portion of the display unit of FIG. 9.

FIGS. 9 and 10 depict yet an exemplary display component 7 according to one embodiment of the present invention. Display component 7 comprises a wrist watch-type display unit which may be worn about the subject's wrist. Display unit 7 includes a flexible band 51 by which the display component may be secured about a subject's wrist. Display component 7 also includes a display screen 52, which may be configured similar to the display screen of a digital wrist watch. Thus, display screen 52 is configured so as to display data and other information to the subject by means of an LCD screen, or other suitable means well-known to those skilled in the art. Display component 7 further includes actuators or switches 53–56 which allow the subject to operate and control the monitoring system of the present invention. Display screen 52 also may be subdivided into a number of regions which are configured to display specific information to the subject. For example, first display region 70 may be configured as a three digit display which provides the subject's blood oxygen level (as a percentage of saturation) or the subject's heart rate (in beats per minute). Second display region 71 is similarly configured as a three digit display, which may be used to display the subject's velocity (in miles per hour or kilometers per hour) or the subject's pace (e.g., in minutes per mile). A third display region 72 is also shown, and may be configured to display, for example, elapsed time.

Display screen 52 also includes first and second status indicators 57 and 58. Status indicators 57 and 58 may be configured such that status indicator 57 will illuminate when the GPS device has acquired the necessary satellite signals for measurement purposes. Second status indicator 58 may similarly illuminate when the sensor or probe for the physiological monitor (such as an oximeter or heart rate monitor) is operable and acquiring physiological data from the subject. First and second mode indicator 73 and 74 may also be provided on display screen 52. First mode indicator 73 merely indicates to the subject the current mode of operation of display component 7. During use, the subject may alter the mode of operation of display component 7 in order to alter the particular data or other information displayed on display screen 52. The subject may utilize mode switch 54 to toggle display screen 52 so as to display one or more of the following data: blood oxygen level, heart rate, elapsed time ("TM"), average speed, maximum speed, year-to-date miles or kilometers ("YTD"), or the current time ("clock mode" or "CL"). Second mode indicator 74 merely indicates to the subject whether or not data is being displayed in terms of miles per hour, kilometers per hour, or minutes per mile.

In order to operate display component 7, a number of actuators or switches are provided. Thus, as mentioned above, mode switch 54 is used to toggle display screen 52 between various modes of operation. Start/stop switch 53 may be used to commence data measurement. For example, the subject may press start/stop switch 53 when they begin performing a physical activity such that the measurement of elapsed time and distance traveled will begin at that point. When the start/stop switch 53 is depressed a second time, measurement of elapsed time and distance traveled will stop, similar to the manner in which a chronograph is employed. Display component 7 also includes third and fourth actuators 55 and 56 positioned on either side of display screen 52. Actuators 55 and 56 may be used for a variety of purposes, depending upon the configuration of the monitoring system. For example, actuator 55 may be used to toggle first display region 70 between displaying blood oxygen level and heart rate. Similarly, actuator 56 may be used to toggle second display region 71 between displaying miles per hour, kilometers per hour, or minutes per mile.

Figure 13:
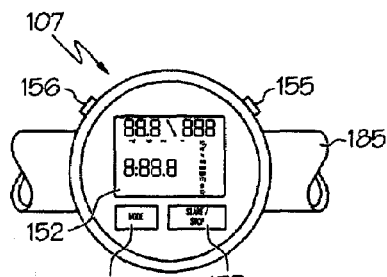
FIG. 13 depicts an alternative display unit according to an embodiment of the exercise monitoring system of the present invention, wherein the display unit is mounted to a handlebar of a bicycle.
Figure 14:
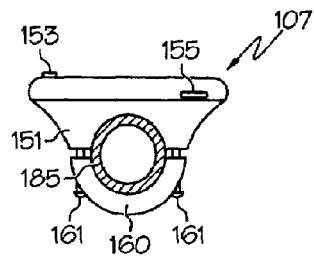
FIG. 14 is a side view of the display unit of FIG. 13, wherein the bicycle handlebar is shown in cross-section.

FIGS. 13 and 14 depict an alternative display unit 107 which is configured to be mounted on a bicycle such that a subject riding the bicycle can view the data displayed on display unit 107. Display unit 107 includes a main housing 151 and a clamp member 160 positioned beneath main housing 151. Main housing 151 and clamp member 160 each include a semi-circular groove such that when main housing 151 and clamp member 160 are positioned as shown in FIG. 14, a circular opening is provided therebetween. This circular opening is sized an configured to accept a handlebar 185 of a bicycle. In this manner, when clamp member 160 is secured to main housing 151 (such as by means of screws 161), handlebar 185 is securely held between clamp member 160 and main housing 151 as shown.

Display unit 107 further includes a display screen 152 which may be configured in the same manner as display screen 52 of the display unit shown in FIG. 10. Display unit 107 also includes input switches 15–156, which may be configured in the same manner as input switches 53–56 on the display unit shown in FIG. 10. Thus, display unit 107 is essentially the same as display unit 7 of FIG. 10, except that the clamping mechanism described above has replaced band 51, of the display unit shown in FIG. 7. It should be noted that band 51 of display unit 7 of FIG. 10 may also be used to secure display unit 7 to the handlebars of a bicycle, particular if band 51 employs a hook and loop fastening system.

Analytical and Training Methods

While the monitoring system of the present invention may simply display the exercising subject's location (e.g., in terms of longitude and latitude), altitude, velocity, pace, heart rate (e.g., in beats per minute), distance traveled, and/or blood oxygen level (e.g., as a percentage of saturation), the monitoring system of the present invention may be configured to further process, analyze or otherwise utilize this data. In this manner, the monitoring systems of the present invention may be used to monitor, analyze and/or control a subject's performance of a physical activity at any location.

By way of example, runners are very interested in monitoring their velocity, pace and/or total distance run. A simple pedometer may provide a rough estimate of the total distance run, however, such devices are inaccurate and do not provide a direct measurement of velocity or pace. While treadmills typically provide an accurate measurement of velocity, pace and total distance, many runners prefer outdoor running. Running on a track or premeasured route will also provide a measure of total distance run, however, many runners do not want to be restricted to running round and round on a track or on the same course day after day. In addition, the runner will be unable to determine their instantaneous velocity, pace or total distance traveled.

In order to overcome the above problems, the monitoring systems of the present invention which include a GPS device may be configured to provide more than just location information. As described previously, the location data acquired by the GPS device may be used to compute and display the subject's velocity, pace and/or distance traveled. Such information is particularly useful when the subject is performing a physical activity wherein performance may be measured in terms of speed, time and/or distance, such as walking, running, swimming, wheelchairing (e.g., wheel chair racing), bicycling, skating (e.g., speed skating on any surface), skiing (e.g., cross-country skiing), or boating (e.g., rowing, sailing, kayaking, or canoeing), or climbing (e.g., rock climbing). When the system is worn by a human subject performing a physical activity, he or she may simply view the display screen at any time in order to obtain their speed, pace and/or distance traveled. Alternatively, particularly when the subject is an animal such as a horse, the display screen may be viewed by another individual (such as a trainer or even a jockey) in order to monitor the animal's speed, pace and/or distance traveled.

A monitoring system according to one embodiment of the present invention may also be configured (e.g., programmed) to provide a visual and/or audible alarm which is responsive to data provided by the GPS device and/or a physiological monitor (when provided). In one embodiment, the system is user-programmable so that a visible and/or audible alarm is activated when at least one of the subject's speed, pace, blood oxygen level and heart rate departs from a predetermined target, and/or when the subject has traveled a predetermined target distance. For example, a runner may input a predetermined pace of 6:00 per mile (a pace "set point"). Thereafter, the system alarm will activate whenever the runner's pace departs from the desired 6:00 per mile pace by more than a certain amount (e.g., ±10%). The alarm will remain activated until the runner's pace returns to the desired level. The runner may also input a predetermined distance. Thereafter, the system alarm will activate when the runner has traveled this predetermined distance. In this manner, the runner can precisely control their speed and/or total distance without having to run on a treadmill or track.

The monitoring system may also be configured such that multiple targets (or set points) may be established by a user (e.g., the subject performing the physical activity, or a coach or trainer). For example, a runner may wish to perform interval training wherein they maintain a first predetermined pace for a first predetermined period of time or distance, and thereafter maintain a second predetermined pace for a second predetermined period of time or distance. Thus, the monitoring system of the present invention may be configured to allow for the input of multiple setpoints (or targets) and multiple time or distance intervals. Thereafter, a system alarm will activate when the runner's pace departs from a specified setpoint of a particular interval, thereby allowing the runner to perform interval training at precise speeds and/or distances.

The systems of the present invention may also be configured for recording speed, pace and/or distance traveled data, and maintaining such data in memory for later retrieval and/or display. For example, the start button (or other input device) may be activated in order to commence recording of data (such as to coincide with beginning performance of the physical activity). The stop button (or other input device) may thereafter be activated upon completion of the physical activity. Speed, pace, average speed, average pace, elapsed time and/or distance traveled data may then be retrieved from memory and displayed.

When the system of the present invention includes both a GPS device and a physiological monitor, data provided by the GPS device may be used in conjunction with data provided by the physiological monitor. While heart rate and blood oxygen data is useful, the utility of such data is greatly improved if the subject's workload is also known. Thus, embodiments of the monitoring system of the present invention which includes both a GPS device and a physiological monitor allow for the monitoring of a physiological parameter (e.g., heart rate or blood oxygen level) and workload. A user may even input their weight so that the monitoring system may compute real-time workload based upon the subject's velocity and altitude changes. In this manner, the system even accounts for elevational changes when determining (and even displaying) the subject's workload. Thus, meaningful data can be obtained even when the subject is exercising at varying altitudes (e.g., running or biking on hilly terrain).

Applicants have also found that monitoring blood oxygen levels while performing a physical activity provides data which is useful for both training and analytical purposes. For example, applicants believe that blood oxygen data provides an indicia of metabolic function, and therefore provides an effective training parameter which can replace or be used in conjunction with heart rate monitoring. As further described below, blood oxygen monitoring also allows for training and analytical techniques which are generally difficult to implement using conventional physiological monitoring such as heart rate monitoring.

As an individual performs a physical activity, the working muscles consume oxygen at a rate which is higher than the rate of oxygen consumption while at rest. The body compensates for the increased oxygen requirements by increasing oxygen intake and/or blood flow. Oxygen intake may be increased, for example, by increasing breathing rate and/or the volume of air inhaled in each breath, while blood flow is increased by an increase in heart rate. At low levels of physical exertion, the blood oxygen level will remain at or near the subject's normal resting level. At these low levels of exertion, energy is primarily provided by an aerobic metabolic process which consumes oxygen. Since the cardiovascular system is able to supply sufficient oxygen to meet the body's demands, blood oxygen level remains at or near the normal resting levels.

As the level of exertion is increased, however, the cardiovascular system is unable to supply sufficient oxygen to meet the demands of working muscles. Thus, the body will begin to supply a portion of the energy requirements by an anaerobic metabolic process which does not consume oxygen. However, lactic acid is a byproduct of the anaerobic process, and must be eliminated by the body in order to prevent muscle failure. When only a small portion of the subject's energy requirements are provided by the anaerobic process, the body is generally able to eliminate the lactic acid byproduct. As the level of exertion is increased, however, the anaerobic process is responsible for more and more of the body's energy requirements. Eventually, the body is unable to eliminate lactic acid at the same rate that it is being produced. At this point (often referred to as the "lactate threshold" or "LT"), lactic acid will begin to accumulate in the working muscles, eventually leading to muscle failure. If the subject continues to perform at a level of exertion above LT, it is only a matter of time until the working muscles begin to fail and the subject must stop.

Figure 16:
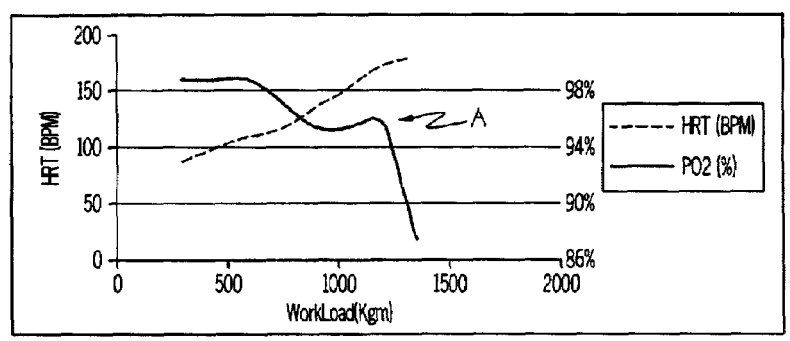
FIG. 16 is a plot which depicts a runner's heart rate and blood oxygen level as the runner's workload is progressively increased.

Applicants have surprisingly found that blood oxygen data provides an indirect measurement of the body's metabolic functioning. For example, as the level of exertion is progressively increased, the blood oxygen level will decrease. The plot shown in FIG. 16 depicts a runner's heart rate and blood oxygen level as their workload is progressively increased. Workload can easily be computed on the basis of the subject's weight and speed (and optionally altitude changes if running on a hilly course), and the monitoring system of the present invention can readily compute and display the subject's workload. As noted from the plot FIG. 16, heart rate increases with workload, while blood oxygen level decreases. Thus, it is apparent that blood oxygen level (particularly systemic blood oxygen level) varies with the metabolic functioning of the body. In fact, Applicants' discovery that blood oxygen level provides an indicator of metabolic function is quite useful in that blood oxygen data can now be used to monitor, analyze and/or control a subject's performance of a physical activity. Thus, the present invention provides methods using blood oxygen data to perform one or more of these functions. In fact, embodiments of the monitoring system of the present invention may be configured (e.g., programmed) to provide one or more of these functions (such as activating an alarm when the subject's blood oxygen level departs from a predetermined target level or range). It should be pointed out, however, that the methods of the present invention which utilize blood oxygen data need not be performed using the exercise monitoring systems of the present invention.

One particular method provided by the present invention is a method of controlling (i.e., regulating) a subject's physical activity by monitoring the subject's blood oxygen level, and maintaining the subject's blood oxygen level at a selected level (such as a setpoint or a range) while the subject continues to perform the physical activity. Such a method can provide an effective training tool for athletes in that they (or their coaches) can more effectively control training sessions, or even monitor their performance during a race. For example, if a marathoner knows their appropriate blood oxygen level for completing a marathon, they can monitor their blood oxygen level during the race in order to ensure that their blood oxygen level does not exceed or fall below their target level.

The subject's blood oxygen level can be maintained at a selected level by adjusting the subject's workload (e.g., slowing down, speeding up, changing gears on a bike, etc.). Similarly, the subject's level of exertion may also be modified as needed in order to maintain their blood oxygen level at the selected level. The subject's oxygen intake may even be modified in order to maintain blood oxygen at the selected level. For example, various devices are available for regulating the amount of oxygen which is inhaled by an exercising subject (such as by restricting air flow to the user's lungs). A swimmer can also regulate their oxygen intake by regulating their breathing. Thus, a swimmer can even use the monitoring systems of the present invention (particularly an embodiment having an audible alarm which activates when blood oxygen departs from the selected level) to regulate their blood oxygen by altering breathing patterns. A subject can also control the depth or volume of their breathing (e.g., deep or shallow breathing) in order to maintain blood oxygen at the desired level. The subject's blood oxygen level can also be maintained at a plurality of selected levels for one or more predetermined intervals. Thus, interval training can be performed based upon blood oxygen data.

The subject may also perform initial testing in order to determine desirable blood oxygen levels or heart rate for subsequent training or competition. For example, the subject may perform a test routine which estimates the subject's lactate threshold (i.e., the subject's blood oxygen level or heart rate at their lactate threshold). Thereafter, the subject may perform a physical activity at a blood oxygen level which is selected on the basis of their previously determined lactate threshold ("LT"). By way of example, the subject's LT may be determined using a plot similar to that of FIG. 16. The subject performs a physical activity while their blood oxygen level is monitored. The subject's workload (e.g., speed) is then incrementally increased at predetermined intervals (e.g., increase speed by 1% every two minutes) until exhaustion (or some other selected endpoint). When blood oxygen is plotted against workload (or even speed), the subject's LT will generally correspond to the point of inflection identified at A in FIG. 16.

As yet another alternative, a fitness parameter (such as LT) of a subject may first be determined. Thereafter, the same fitness parameter may be measured on subsequent occasions in order to measure improvements in the subject's fitness.

The monitoring system of the present invention described above may even be programmed to provide for determining a fitness indicator (such as LT). The subject's weight may be inputted into the system, and the subject will then begin performing the physical activity (e.g., running). The system may determine the subject's speed and altitude changes, which the system then uses to calculate the subject's workload. The system may even be programmed to signal to the subject when the workload should be increased (such as by activating an alarm). Once the test protocol has been completed, the system will calculate the subject's LT (or other fitness indicator) on the basis of the acquired workload and blood oxygen data. Alternatively, the system may use heart rate (rather than blood oxygen data) to compute the fitness indicator (such as LT) by well-known methods. One such well-known test protocol is the Conconi Test which employs heart rate measurements with increasing workload to determine a subject's VO2max.

Blood oxygen data can also be monitored while a subject performs a physical activity in order to reduce variability in blood oxygen levels. By stabilizing blood oxygen levels while performing at a constant workload, the subject's performance will be improved. Thus, the monitoring system of the present invention may be configured to measure the time variability of the subject's blood oxygen level, particularly when the workload remains at a substantially constant level. The time variability may simply be calculated as the standard deviation of blood oxygen over a predetermined time interval (e.g., the standard deviation of blood oxygen level over the preceding 5 seconds). The manner in which the physical activity is performed may then be adjusted in order to reduce the time variability of blood oxygen level. In fact, the system may even be configured to activate an alarm if the time variability of the subject's blood oxygen level exceeds a predetermined limit. By way of example, the subject may reduce the time variability of blood oxygen by stabilizing their breathing (e.g., concentrating on deep, rhythmic breathing), or by merely concentrating on stabilizing their workload or level of exertion.

Figure 17A:
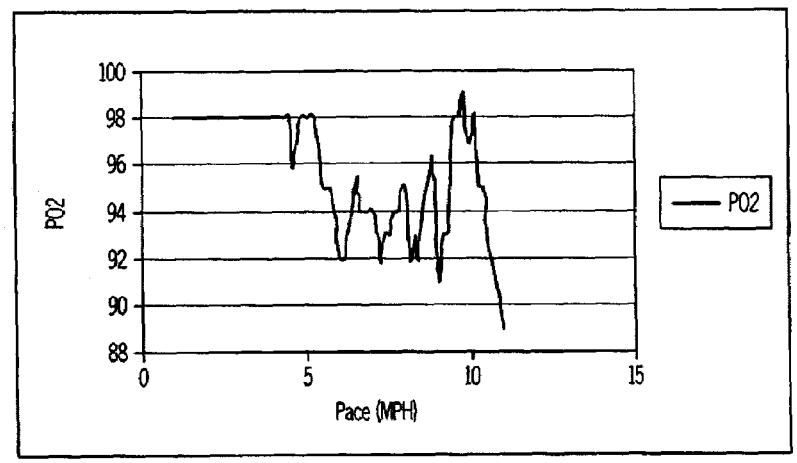
FIGS. 17a and 17b are plots depicting a runner's blood oxygen level as the runner's pace is progressively increased.
Figure 17B:
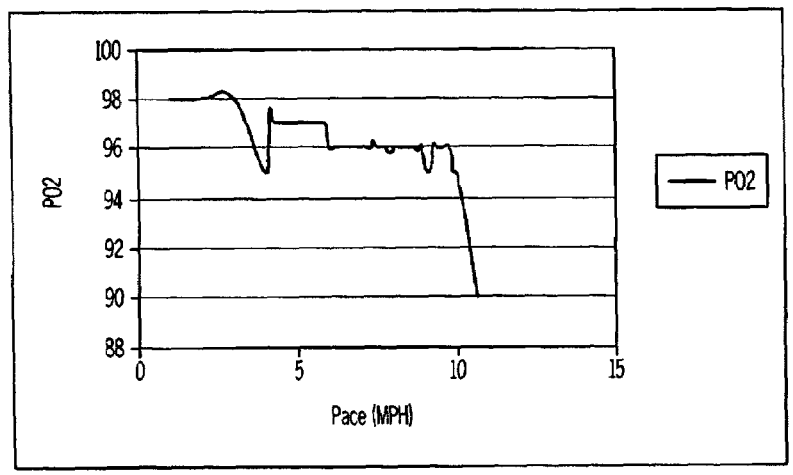

By way of example, the plot of FIG. 17a depicts a runner's blood oxygen level as their pace (in miles per hour) is gradually increased. It will be noted that the subject's blood oxygen level shows significant variability which does not correlate with increases in workload. In other words, the subject's blood oxygen level shows significant peaks and valleys, rather than gradually decreasing as would be expected. When blood oxygen level drops and rises rapidly, the subject's performance will suffer. For example, lactate levels may begin to rise, leading to premature muscle failure. FIG. 17b is a plot from the same runner, however the runner concentrated on their breathing (i.e., rhythmic, deep breathing from their belly, rather than from their chest). The result is that blood oxygen levels are more stable, even though the workload is increasing. In fact, the subject's blood oxygen level in FIG. 17b remained substantially constant at about 96% when pace was increased from about 6 mph to about 9 mph. In the plot of FIG. 17a, however, the subject's blood oxygen level varied between about 91% and about 98% over this same pace range. Such variability in blood oxygen level will inevitably lead to decreased performance.

The invention claimed is:

1. A method of controlling a subjects physical activity, comprising:
    (a) monitoring a subject's blood oxygen level while the subject performs a physical activity; and
    (b) maintaining said blood oxygen level at a selected level while the subject continues to perform said physical activity.

2. The method of claim 1, wherein said blood oxygen level is maintained at said selected level by adjusting the workload of said physical activity as necessary.

3. The method of claim 1, wherein said blood oxygen level is maintained at said selected level by adjusting the subject's level of exertion as necessary.

4. The method of claim 1, wherein said blood oxygen level is maintained at said selected level by adjusting the subject's oxygen intake as necessary.

5. The method of claim 1, wherein said physical activity is chosen from the group consisting of: walking, running, swimming, bicycling, skating, singing, skiing, boating, climbing, wheelchairing, snowshoeing, scuba diving, and flying.

6. The method of claim 1, wherein said step of monitoring blood oxygen level comprises:
    (a) providing an oximeter, said oximeter including a probe for non-invasively determining blood oxygen level; and
    (b) positioning said probe on said subject at a location suitable for detecting the subject's blood oxygen level.

7. The method of claim 6, wherein said probe is positioned such that said oximeter determines the subject's systemic blood oxygen level.

8. The method of claim 4, wherein said blood oxygen level is maintained at each selected level:
    (a) for a predetermined period of time;
    (b) until the subject has advanced a predetermined distance; or
    (c) until the subject has performed a predetermined amount of work.

9. The method of claim 1, wherein said selected level is chosen on the basis of blood oxygen data previously obtained while said subject performed a physical activity.

10. The method of claim 1, wherein said selected level is chosen on the basis of said subject's lactate threshold.

11. The method of claim 1, wherein said selected level is chosen on the basis of the duration of said physical activity.

12. The method of claim 1, further comprising the step of providing an alarm, said alarm configured for indicating when the subject's blood oxygen level is not at said selected level.

13. The method of claim 1, further comprising the step of providing a display unit configured for displaying the subject's blood oxygen level.

14. The method of claim 13, wherein said subject comprises a human, and said display unit is positioned so that the blood oxygen level displayed by said display unit can be viewed by said subject.

15. The method of claim 14, wherein said physical activity comprises bicycling, and said display unit is attached to the subject's bicycle so as to be visible to the subject.

16. The method of claim 1, further comprising the step of measuring at least one of the subject's velocity, pace, or distance traveled.

17. The method of claim 16, wherein said measuring step comprises:

providing a GPS device operable for measuring at least one of the subject's velocity, pace or distance traveled.

18. The method of claim 16, further comprising the step of providing a display unit configured for displaying the subject's blood oxygen level, and at least one of the subject's velocity, pace or distance traveled.

19. A method of reducing a subject's blood oxygen level variability while the subject performs a physical activity, comprising:

(a) periodically measuring a subject's blood oxygen level while said subject performs a physical activity; and (b) adjusting the manner in which said physical activity is performed in order to reduce blood oxygen level variability.

20. A method of determining a fitness indicator of a subject, comprising:

(a) recording a subject's blood oxygen level while the subject performs a physical activity;

(b) varying the subject's workload while continuing to record the subject's blood oxygen level; and (c) determining a fitness indicator of said subject on the basis of the recorded blood oxygen data.

* * * * *